US011530402B2

(12) United States Patent
Xiao et al.

(10) Patent No.: US 11,530,402 B2
(45) Date of Patent: Dec. 20, 2022

(54) OPTIMIZED HUMAN CLOTTING FACTOR IX GENE EXPRESSION CASSETTES AND THEIR USE

(71) Applicant: The University of North Carolina at Chapel Hill, Chapel Hill, NC (US)

(72) Inventors: Xiao Xiao, Chapel Hill, NC (US); Juan Li, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/616,784

(22) PCT Filed: May 31, 2018

(86) PCT No.: PCT/US2018/035267
§ 371 (c)(1),
(2) Date: Nov. 25, 2019

(87) PCT Pub. No.: WO2018/222792
PCT Pub. Date: Dec. 6, 2018

(65) Prior Publication Data
US 2020/0087646 A1    Mar. 19, 2020

Related U.S. Application Data

(60) Provisional application No. 62/512,833, filed on May 31, 2017.

(51) Int. Cl.
*C12N 9/64* (2006.01)
*C12N 15/86* (2006.01)
*A61P 7/04* (2006.01)
*A61K 48/00* (2006.01)

(52) U.S. Cl.
CPC .......... *C12N 9/644* (2013.01); *A61K 48/0058* (2013.01); *A61P 7/04* (2018.01); *C12N 15/86* (2013.01); *C12Y 304/21022* (2013.01)

(58) Field of Classification Search
None
See application file for complete search history.

(56) References Cited

U.S. PATENT DOCUMENTS

| 8,030,065 B2 | 10/2011 | Gray |
| 2007/0042462 A1 | 2/2007 | Hildinger |

FOREIGN PATENT DOCUMENTS

| EP | 2021499 | 2/2009 |
| RU | 2585532 | 5/2016 |
| WO | 2007/078599 | 7/2007 |
| WO | 2009/130208 | 10/2009 |
| WO | 2015138348 A1 | 9/2015 |
| WO | 2016/210170 | 12/2016 |
| WO | WO-2017180861 A1 * 10/2017 ......... A61K 48/0058 |

OTHER PUBLICATIONS

International Preliminary Report on Patentability corresponding to International Application No. PCT/US2018/035267 dated Dec. 12, 2019.
"Extended European Search Report corresponding to European Application No. 18809332.2 dated Feb. 19, 2021".
International Search Report and Written Opinion corresponding to International Application No. PCT/US2018/035267 dated Oct. 25, 2018.
Accession No. JS560043.1, GQY7JOC02FW137counts=1 Gao AAV mouse Integration Site Library Mus musculus genomic, genomic survey sequence., Database GenBank [online], Dec. 23, 2011.
"Office Action corresponding to Japanese Application No. 2019-566601 dated Mar. 22, 2022".
"Office Action corresponding to Chinese Application No. 201810547030.2 dated Dec. 3, 2021".
FDA News Release "FDA approves novel gene therapy to treat patients with a rareform of inherited vision loss" https://www.fda.gov/news-events/press-announcements/fda-approves-novel-gene-therapy-treat-patients-rare-form-inherited-vision-loss (4 pages) (Dec. 18, 2017).
George et al. "Hemophilia B Gene Therapy with a High-Specific-Activity Factor IX Variant" The New England Journal of Medicine, 377(23):2215-2227 (Dec. 2017).
Keeler et al. "Gene Therapy 2017: Progress and Future Directions" Clinical and Translational Science, 10:242-248 (May 2017).
Monahan, P. E. "Gene therapy in an era of emerging treatment options for hemophilia B" Journal of Thrombosis and Haemostasis, 13(Suppl. 1):S151-S160 (2015).

\* cited by examiner

*Primary Examiner* — Marsha Tsay
(74) *Attorney, Agent, or Firm* — Myers Bigel, P.A.

(57) ABSTRACT

The invention relates to synthetic liver-specific promoters and expression constructs for producing polypeptides and functional nucleic acids in the liver of a subject. The invention further relates to optimized polynucleotide sequences encoding Factor IX proteins, vector comprising the same, and methods of using these compositions to treat a bleeding disorder.

26 Claims, 2 Drawing Sheets
Specification includes a Sequence Listing.

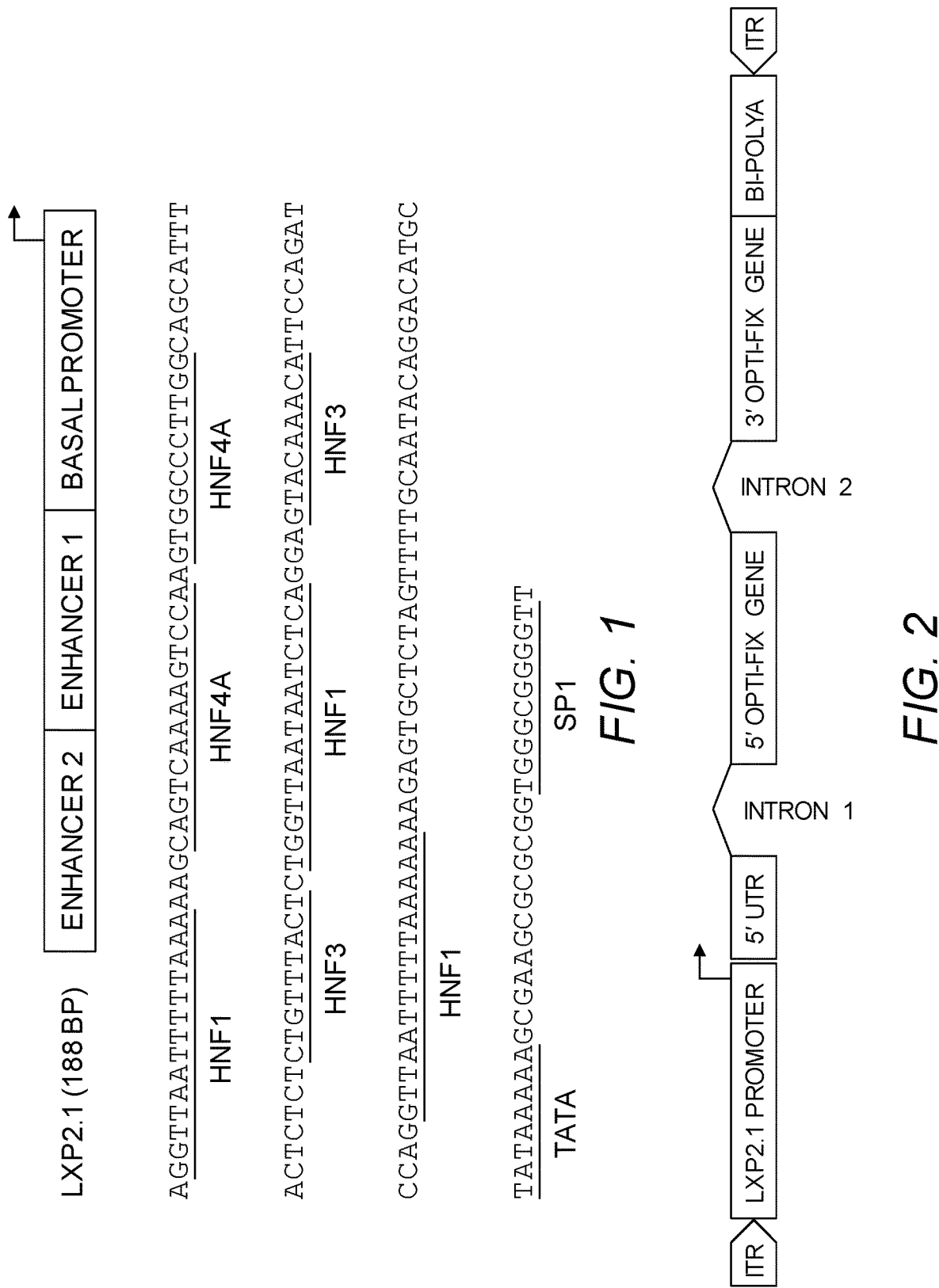

SEQUENCE LISTING

```
<160> NUMBER OF SEQ ID NOS: 16

<210> SEQ ID NO 1
<211> LENGTH: 188
<212> TYPE: DNA
<213> ORGANISM: Artificial Sequence
<220> FEATURE:
<223> OTHER INFORMATION: Promoter LXP2.1
<220> FEATURE:
<221> NAME/KEY: promoter
<222> LOCATION: (1)..(188)

<400> SEQUENCE: 1
aggttaattt ttaaaaagca gtcaaaagtc caagtggccc ttggcagcat ttactctctc      60
tgtttactct ggttaataat ctcaggagta caaacattcc agatccaggt taatttttaa     120
aaaaagagtg ctctagtttt gcaatacagg acatgctata aaaagcgaag cgcgcggtgg     180
gcggggtt                                                               188

<210> SEQ ID NO 2
<211> LENGTH: 359
```

```
<212> TYPE: DNA
<213> ORGANISM: Artificial Sequence
<220> FEATURE:
<223> OTHER INFORMATION: Promoter and 5'UTR and intron-1
<220> FEATURE:
<221> NAME/KEY: promoter
<222> LOCATION: (1)..(188)
<220> FEATURE:
<221> NAME/KEY: 5'UTR
<222> LOCATION: (189)..(263)
<220> FEATURE:
<221> NAME/KEY: Intron
<222> LOCATION: (264)..(351)
<220> FEATURE:
<221> NAME/KEY: 5'UTR
<222> LOCATION: (352)..(359)

<400> SEQUENCE: 2
aggttaattt ttaaaaagca gtcaaaagtc caagtggccc ttggcagcat ttactctctc      60
tgtttactct ggttaataat ctcaggagta caaacattcc agatccaggt taatttttaa     120
aaaaagagtg ctctagtttt gcaatacagg acatgctata aaaagcgaag cgcgcggtgg     180
gcggggttga agctaacaaa gaccacgacg atatcacggt cgtggtctca agaacaaca      240 aacaacaaag tccgactgag aaggtgagtg gcgggccctg agctgggggg cggggtgtt     300 ggctctggag gctgggtctg agcgtaattt tgcaccccg cgtccctgca ggagccacc      359

<210> SEQ ID NO 3
<211> LENGTH: 83
<212> TYPE: DNA
<213> ORGANISM: Artificial Sequence
<220> FEATURE:
<223> OTHER INFORMATION: 5' untranslated UTR
<220> FEATURE:
<221> NAME/KEY: 5'UTR
<222> LOCATION: (1)..(83)

<400> SEQUENCE: 3
gaagctaaca aagaccacga cgatatcacg gtcgtggtct caaagaacaa caaacaacaa      60
agtccgactg agaaggagcc acc                                             83

<210> SEQ ID NO 4
<211> LENGTH: 171
<212> TYPE: DNA
<213> ORGANISM: Artificial Sequence
<220> FEATURE:
<223> OTHER INFORMATION: 5' UTR and intron-1
<220> FEATURE:
<221> NAME/KEY: 5'UTR
<222> LOCATION: (1)..(77)
<220> FEATURE:
<221> NAME/KEY: Intron
<222> LOCATION: (78)..(161)
<220> FEATURE:
<221> NAME/KEY: 5'UTR
<222> LOCATION: (162)..(171)

<400> SEQUENCE: 4
gaagctaaca aagaccacga cgatatcacg gtcgtggtct caaagaacaa caaacaacaa      60
agtccgactg agaaggtgag tggcgggccc tgagctgggg ggcggggtg ttggctctgg     120 aggctgggtc tgagcgtaat tttgcacccc cgcgtccctg caggagccac c              171

<210> SEQ ID NO 5
<211> LENGTH: 82
<212> TYPE: DNA
<213> ORGANISM: Artificial Sequence
<220> FEATURE:
```

<223> OTHER INFORMATION: de novo inserted intron-2
<220> FEATURE:
<221> NAME/KEY: Intron
<222> LOCATION: (1)..(82)

<400> SEQUENCE: 5

```
gtgagtatct cagggatcca gacatgggga tatgggaggt gcctctgatc ccagggctca    60
ctgtgggtct ctctgttcac ag                                              82
```

<210> SEQ ID NO 6
<211> LENGTH: 1471
<212> TYPE: DNA
<213> ORGANISM: Artificial Sequence
<220> FEATURE:
<223> OTHER INFORMATION: Codon optimized human factor IX gene-1 with
      artificial intron-2
<220> FEATURE:
<221> NAME/KEY: Intron
<222> LOCATION: (129)..(210)

<400> SEQUENCE: 6

```
atgcagaggg tgaacatgat catggctgag agccctggcc tgatcaccat ctgcctgctg    60
ggctacctgc tgtctgctga gtgcactgtg ttcctggacc atgagaatgc caacaagatc   120
ctgaacaggt gagtatctca gggatccaga catggggata tgggaggtgc ctctgatccc   180
agggctcact gtgggtctct ctgttcacag gcccaagaga tacaactctg caagctgga    240 ggagtttgtg cagggcaacc tggagaggga gtgcatggag agaagtgca gctttgagga    300 ggccagggag tgtttgaga acactgagag gaccactgag ttctggaagc agtatgtgga   360
tggggaccag tgtgagagca cccctgcct gaatggggc agctgcaagg atgacatcaa    420
cagctatgag tgctggtgcc cctttggctt tgagggcaag aactgtgagc tggatgtgac    480
ctgcaacatc aagaatggca gatgtgagca gttctgcaag aactctgctg acaacaaggt   540
ggtgtgcagc tgcactgagg ctacaggct ggctgagaac cagaagagct gtgagcctgc    600
tgtgccattc ccatgtggca gagtgtctgt gagccagacc agcaagctga ccagggctga    660
ggctgtgttc cctgatgtgg actatgtgaa cagcactgag gctgaaacca tcctggacaa    720
catcacccag agcaccccaga gcttcaatga cttcaccagg gtggtggggg gggaggatgc    780
caagcctggc cagttcccct ggcaagtggt gctgaatggc aaggtggatg ccttctgtgg    840
gggcagcatt gtgaatgaga gtggattgt gactgctgcc cactgtgtgg agactggggt    900
gaagatcact gtggtggctg gggagcacaa cattgaggag actgagcaca ctgagcagaa    960
gaggaatgtg atcaggatca ccccccacca caactacaat gctgccatca acaagtacaa   1020
ccatgacatt gccctgctgg agctggatga gccccctggtg ctgaacagct atgtgacccc   1080
catctgcatt gctgacaagg agtacaccaa catcttcctg aagtttggct ctggctatgt   1140
gtctggctgg ggcagggtgt ccacaagggg caggtctgcc ctggtgctgc agtacctgag   1200
ggtgcccctg gtgacaggg ccacctgcct gctgagcacc aagttcacca tctacaacaa   1260
catgttctgt gctggcttcc atgagggggg cagggacagc tgccagggg actctggcgg   1320 cccccatgtg actgaggtgg agggcaccag cttcctgact ggcatcatca gctgggggga   1380
ggagtgtgcc atgaagggca gtatggcat ctacaccaaa gtctccagat atgtgaactg   1440
gatcaaggag aagaccaagc tgacctgata a                                   1471
```

<210> SEQ ID NO 7
<211> LENGTH: 1471
<212> TYPE: DNA

<213> ORGANISM: Artificial Sequence
<220> FEATURE:
<223> OTHER INFORMATION: Codon optimized human factor IX gene-2 with
      artificial intron-2
<220> FEATURE:
<221> NAME/KEY: Intron
<222> LOCATION: (172)..(253)

<400> SEQUENCE: 7

```
atgcagaggg tcaacatgat tatggctgag agccctggcc tgatcaccat ctgtctgctg      60
ggctacctgc tgtctgcaga gtgcacagtg tttctggacc atgagaatgc caacaagatc     120
ctgaacaggc ccaagaggta caactctggc aagctggaag agtttgtgca ggtgagtatc     180
tcaggatcc agacatgggg atatgggagg tgcctctgat cccagggctc actgtgggtc      240
tctctgttca cagggcaacc tggaaaggga atgcatggaa gagaagtgca gctttgaaga     300
ggccagggaa gtgtttgaga acacagagag aaccacagag ttctggaagc agtatgtgga     360
tggggaccag tgtgaaagca ccccctgcct gaatggtggc agctgcaagg atgacatcaa     420
cagctatgag tgctggtgcc cctttggctt tgagggcaag aactgtgaac tggatgtgac     480
ctgcaacatc aagaatggca gatgtgaaca gttctgcaag aactctgctg acaacaaggt     540
tgtgtgctcc tgcacagagg gctacagact ggctgagaac cagaaaagct gtgaacctgc     600
tgtgcccttt ccatgtggca gagtgtctgt gtcccagacc agcaagctga ccagagctga     660
ggctgtgttc cctgatgtgg actatgtgaa ctccacagag gctgagacaa tcctggacaa     720
catcacccag agcacccagt ccttcaatga cttcacaaga gttgttggag ggaagatgc      780
caagcctgga cagttccctt ggcaagtggt gctgaatggc aaagtggatg ccttctgtgg     840
tggctccatt gtgaatgaga gtggattgt gacagctgcc cactgtgtgg aaacaggggt      900
caagatcaca gtggtggctg gggagcacaa cattgaggaa acagagcaca cagagcaaaa     960
gaggaatgtc atcaggatca tccctcacca caactacaat gctgccatca caagtacaa    1020
ccatgacatt gccctgcttg agctggatga gcccctggtc ctgaactcct atgtgacccc    1080
tatctgcatt gctgacaaag agtacaccaa catctttctg aagtttggct ctggctatgt    1140
gtctggctgg ggtagagtgt tccacaaggg aagatctgcc ctggtgctgc agtacctgag    1200
agtgcccctg gtggatagag ccacatgtct gctgagcacc aagttccacc tctacaacaa    1260
catgttctgt gctgggttcc atgaaggtgg cagagactcc tgccagggag atagtggtgg    1320
ccctcatgtg acagaggtgg aaggcaccag cttttctgaca ggcatcatca gctggggaga    1380
agagtgtgcc atgaagggca atatggcat ctacaccaag gtgtccagat atgtcaactg     1440
gatcaaagaa aagaccaagc tcacctgata a                                   1471
```

<210> SEQ ID NO 8
<211> LENGTH: 1471
<212> TYPE: DNA
<213> ORGANISM: Artificial Sequence
<220> FEATURE:
<223> OTHER INFORMATION: Codon optimized human factor IX gene-3 with
      artificial intron-2
<220> FEATURE:
<221> NAME/KEY: Intron
<222> LOCATION: (172)..(253)

<400> SEQUENCE: 8

```
atgcagcggg tcaacatgat tatggctgag agccctggcc tgatcaccat ctgtctgctg      60
ggctacctgc tgagcgctga gtgcacagtg tttctggacc atgagaatgc caacaagatc    120
ctgaacaggc ccaagaggta caactctggc aagctggaag agtttgtgca ggtgagtatc    180
```

-continued

```
tcagggatcc agacatgggg atatgggagg tgcctctgat cccagggctc actgtgggtc      240
tctctgttca cagggcaacc tggaaaggga atgcatggaa gagaagtgca gctttgaaga      300
ggcccgggaa gtgtttgaga acacagagcg gaccacagag ttctggaagc agtatgtgga      360
tggggaccag tgtgaaagca accctgtct gaatggcggc agctgcaagg atgacatcaa       420
cagctatgag tgctggtgcc cctttggctt tgagggcaag aactgtgaac tggatgtgac      480
ctgcaacatc aagaatggcc gctgtgaaca gttctgcaag aacagcgctg acaacaaggt      540
tgtgtgctcc tgcacagagg gctacagact ggctgagaac cagaaaagct gtgaacccgc      600
tgtgcccttt ccatgcggca gagtgtctgt gtcccagacc agcaagctga ccagagctga      660
ggctgtgttc cctgatgtgg actatgtgaa cagcacagag gctgagacaa tcctggacaa      720
catcacccag agcacccagt ccttcaatga cttcaccaga gttgttggcg agaggatgc       780 caagcctgga cagttccctt ggcaagtggt gctgaatggc aaagtggatg ccttctgcgg      840
cggcagcatt gtgaatgaga gtggattgt gaccgccgct cactgtgtgg aaaccggggt       900
caagattaca gtggtggccg gggagcacaa cattgaggaa acagagcaca cagagcaaaa      960
gcggaatgtc atccggatca tccctcacca caactacaat gccgccatca acaagtacaa     1020
ccatgacatt gccctgcttg agctggatga gcccctggtc ctgaactcct atgtgacccc     1080
tatctgcatt gctgacaaag agtacaccaa catctttctg aagtttggca gcggctatgt     1140
gtccggctgg ggaagagtgt tccacaaggg aagatctgcc ctggtgctgc agtacctgag     1200 agtgccctg gtggatagag ccacatgtct gctgagcacc aagttcacca tctacaacaa      1260
catgttctgc gccggcttcc atgaaggcgg cagagatagc tgtcagggag attctggcgg     1320
ccctcatgtg acagaggtgg aaggcaccag ctttctgacc ggcatcatca gctggggaga     1380
agagtgtgcc atgaagggca atatggcat ctacaccaag gtgtcccgct atgtcaactg       1440
gatcaaagaa aagaccaagc tcacctgata a                                    1471
```

<210> SEQ ID NO 9
<211> LENGTH: 307
<212> TYPE: DNA
<213> ORGANISM: Artificial Sequence
<220> FEATURE:
<223> OTHER INFORMATION: bi-directional poly A (plus enhancer)
<220> FEATURE:
<221> NAME/KEY: enhancer
<222> LOCATION: (1)..(307)
<220> FEATURE:
<221> NAME/KEY: polyA_signal
<222> LOCATION: (1)..(307)

<400> SEQUENCE: 9

```
tctagatcat aatcagccat accacatttg tagaggtttt acttgcttta aaaaacctcc       60
cacacctccc cctgaacctg aaacataaaa tgaatgcaat tgttgttgtt aacttgttta      120
ttgcagctta taatggttac aaataaagca atagcatcac aaatttcaca aataaagcat      180 tttttttcact gcattctagt tgtggttgt ccaaactcat caatgtatct ggggaggctg      240
ctggtgaata ttaaccaagg tcaccccagt tatcggagga gcaaacaggg gctaagtcca     300
cacgcgt                                                               307
```

<210> SEQ ID NO 10
<211> LENGTH: 2149
<212> TYPE: DNA
<213> ORGANISM: Artificial Sequence
<220> FEATURE:

<223> OTHER INFORMATION: Factor FIX expression cassette-1
<220> FEATURE:
<221> NAME/KEY: promoter
<222> LOCATION: (7)..(194)
<220> FEATURE:
<221> NAME/KEY: 5'UTR
<222> LOCATION: (195)..(269)
<220> FEATURE:
<221> NAME/KEY: Intron
<222> LOCATION: (270)..(357)
<220> FEATURE:
<221> NAME/KEY: 5'UTR
<222> LOCATION: (358)..(365)
<220> FEATURE:
<221> NAME/KEY: Intron
<222> LOCATION: (494)..(575)

<400> SEQUENCE: 10

```
cttaagaggt taattttaa aaagcagtca aaagtccaag tggcccttgg cagcatttac      60
tctctctgtt tactctggtt aataatctca ggagtacaaa cattccagat ccaggttaat   120
ttttaaaaaa agagtgctct agttttgcaa tacaggacat gctataaaaa gcgaagcgcg   180
cggtgggcgg ggttgaagct aacaaagacc acgacgatat cacggtcgtg gtctcaaaga   240
acaacaaaca acaaagtccg actgagaagg tgagtggcgg gccctgagct gggggggcggg   300
ggtgttggct ctggaggctg ggtctgagcg taattttgca ccccccgcgtc cctgcaggag   360
ccaccatgca gagggtgaac atgatcatgg ctgagagccc tggcctgatc accatctgcc   420
tgctgggcta cctgctgtct gctgagtgca ctgtgttcct ggaccatgag aatgccaaca   480
agatcctgaa caggtgagta tctcaggat ccagacatgg ggatatggga ggtgcctctg   540
atcccagggc tcactgtggg tctctctgtt cacaggccca agagatacaa ctctggcaag   600
ctggaggagt ttgtgcaggg caacctggag agggagtgca tggaggagaa gtgcagcttt   660
gaggaggcca gggaggtgtt tgagaacact gagaggacca ctgagttctg gaagcagtat   720
gtggatgggg accagtgtga gagcaacccc tgcctgaatg ggggcagctg caaggatgac   780
atcaacagct atgagtgctg gtgccccttt ggctttgagg gcaagaactg tgagctggat   840
gtgacctgca acatcaagaa tggcagatgt gagcagttct gcaagaactc tgctgacaac   900
aaggtggtgt gcagctgcac tgagggctac aggctgctg agaaccagaa gagctgtgag   960
cctgctgtgc cattcccatg tggcagagtg tctgtgagcc agaccagcaa gctgaccagg   1020
gctgaggctg tgttccctga tgtggactat gtgaacagca ctgaggctga aaccatcctg   1080
gacaacatca cccagagcac ccagagcttc aatgacttca ccagggtggt ggggggggag   1140
gatgccaagc ctggccagtt ccctggcaa gtggtgctga atggcaaggt ggatgccttc   1200
tgtgggggca gcattgtgaa tgagaagtgg attgtgactg ctgcccactg tgtggagact   1260
ggggtgaaga tcactgtggt ggctggggag cacaacattg aggagactga gcacactgag   1320
cagaagagga atgtgatcag gatcatcccc caccacaact acaatgctgc catcaacaag   1380
tacaaccatg acattgccct gctggagctg atgagcccc tggtgctgaa cagctatgtg   1440
accccccatct gcattgctga caaggagtac accaacatct tcctgaagtt tggctctggc   1500
tatgtgtctg gctggggcag ggtgttccac aagggcaggt ctgccctggt gctgcagtac   1560
ctgagggtgc cctggtgga cagggccacc tgcctgctga gcaccaagtt caccatctac   1620
aacaacatgt tctgtgctgg cttccatgag gggggcaggg acagctgcca gggggactct   1680
ggcggccccc atgtgactga ggtggagggc accagcttcc tgactggcat catcagctgg   1740
ggggaggagt gtgccatgaa gggcaagtat ggcatctaca ccaaagtctc cagatatgtg   1800
```

-continued

```
aactggatca aggagaagac caagctgacc tgataagcta gctctagatc ataatcagcc    1860
ataccacatt tgtagaggtt ttacttgctt taaaaaacct cccacacctc cccctgaacc    1920
tgaaacataa aatgaatgca attgttgttg ttaacttgtt tattgcagct tataatggtt    1980
acaaataaag caatagcatc acaaatttca caaataaagc attttttca ctgcattcta     2040 gttgtggttt gtccaaactc atcaatgtat ctggggaggc tgctggtgaa tattaaccaa    2100
ggtcacccca gttatcggag gagcaaacag gggctaagtc cacacgcgt                2149
```

<210> SEQ ID NO 11
<211> LENGTH: 2149
<212> TYPE: DNA
<213> ORGANISM: Artificial Sequence
<220> FEATURE:
<223> OTHER INFORMATION: Factor FIX expression cassette-2
<220> FEATURE:
<221> NAME/KEY: promoter
<222> LOCATION: (7)..(194)
<220> FEATURE:
<221> NAME/KEY: 5'UTR
<222> LOCATION: (195)..(269)
<220> FEATURE:
<221> NAME/KEY: Intron
<222> LOCATION: (270)..(357)
<220> FEATURE:
<221> NAME/KEY: 5'UTR
<222> LOCATION: (358)..(365)
<220> FEATURE:
<221> NAME/KEY: Intron
<222> LOCATION: (537)..(618)

<400> SEQUENCE: 11

```
cttaagaggt taattttaa aaagcagtca aaagtccaag tggcccttgg cagcatttac       60
tctctctgtt tactctggtt aataatctca ggagtacaaa cattccagat ccaggttaat     120
ttttaaaaaa agagtgctct agttttgcaa tacaggacat gctataaaaa gcgaagcgcg     180
cggtgggcgg ggttgaagct aacaaagacc acgacgatat cacggtcgtg gtctcaaaga     240
acaacaaaca acaaagtccg actgagaagg tgagtggcgg gccctgagct gggggcggg     300 ggtgttggct ctggaggctg ggtctgagcg taattttgca ccccgcgtc cctgcaggag     360 ccaccatgca gagggtcaac atgattatgg ctgagagccc tggcctgatc accatctgtc     420
tgctgggcta cctgctgtct gcagagtgca cagtgtttct ggaccatgag aatgccaaca     480
agatcctgaa caggcccaag aggtacaact ctggcaagct ggaagagttt gtgcaggtga     540
gtatctcagg gatccagaca tggggatatg ggaggtgcct ctgatcccag ggctcactgt     600
gggtctctct gttcacaggg caacctggaa agggaatgca tggaagagaa gtgcagcttt     660
gaagaggcca gggaagtgtt tgagaacaca gagagaacca cagagttctg gaagcagtat     720
gtggatgggg accagtgtga aagcaacccc tgcctgaatg gtggcagctg caaggatgac     780
atcaacagct atgagtgctg gtgccccttt ggctttgagg gcaagaactg tgaactggat     840
gtgacctgca acatcaagaa tggcagatgt gaacagttct gcaagaactc tgctgacaac     900
aaggttgtgt gctcctgcac agagggctac agactggctg agaaccagaa agctgtgaa     960 cctgctgtgc cctttccatg tggcagagtg tctgtgtccc agaccagcaa gctgaccaga    1020
gctgaggctg tgttccctga tgtggactat gtgaactcca cagaggctga cacaatcctg    1080
gacaacatca cccagagcac ccagtccttc aatgacttca aagagttgt ggagggggaa     1140 gatgccaagc ctggacagtt ccctggcaa gtggctga atggcaaagt ggatgccttc      1200
tgtggtggct ccattgtgaa tgagaagtgg attgtgacag ctgcccactg tgtggaaaca    1260
```

-continued

```
ggggtcaaga tcacagtggt ggctggggag cacaacattg aggaaacaga gcacacagag    1320
caaaagagga atgtcatcag gatcatccct caccacaact acaatgctgc catcaacaag    1380
tacaaccatg acattgccct gcttgagctg gatgagcccc tggtcctgaa ctcctatgtg    1440 accctatct gcattgctga caaagagtac accaacatct ttctgaagtt tggctctggc    1500
tatgtgtctg gctggggtag agtgttccac aagggaagat ctgccctggt gctgcagtac    1560
ctgagagtgc ccctggtgga tagagccaca tgtctgctga gcaccaagtt caccatctac    1620
aacaacatgt tctgtgctgg gttccatgaa ggtggcagag actcctgcca gggagatagt    1680
ggtggccctc atgtgacaga ggtggaaggc accagctttc tgacaggcat catcagctgg    1740
ggagaagagt gtgccatgaa gggcaaatat ggcatctaca ccaaggtgtc cagatatgtc    1800
aactggatca agaaaagac caagctcacc tgataagcta gctctagatc ataatcagcc    1860
ataccacatt tgtagaggtt ttacttgctt taaaaaacct cccacacctc ccctgaacc    1920 tgaaacataa aatgaatgca attgttgttg ttaacttgtt tattgcagct tataatggtt    1980
acaaataaag caatagcatc acaaatttca caaataaagc attttttca ctgcattcta    2040 gttgtggttt gtccaaactc atcaatgtat ctggggaggc tgctggtgaa tattaaccaa    2100 ggtcaccccca gttatcggag gagcaaacag gggctaagtc cacacgcgt              2149

<210> SEQ ID NO 12
<211> LENGTH: 2149
<212> TYPE: DNA
<213> ORGANISM: Artificial Sequence
<220> FEATURE:
<223> OTHER INFORMATION: Factor FIX expression cassette-3
<220> FEATURE:
<221> NAME/KEY: promoter
<222> LOCATION: (7)..(194)
<220> FEATURE:
<221> NAME/KEY: 5'UTR
<222> LOCATION: (195)..(269)
<220> FEATURE:
<221> NAME/KEY: Intron
<222> LOCATION: (270)..(357)
<220> FEATURE:
<221> NAME/KEY: 5'UTR
<222> LOCATION: (358)..(365)
<220> FEATURE:
<221> NAME/KEY: Intron
<222> LOCATION: (537)..(618)

<400> SEQUENCE: 12
cttaagaggt taattttaa aaagcagtca aaagtccaag tggcccttgg cagcatttac      60
tctctctgtt tactctggtt aataatctca ggagtacaaa cattccagat ccaggttaat    120
ttttaaaaaa agagtgctct agttttgcaa tacaggacat gctataaaaa gcgaagcgcg    180
cggtgggcgg ggttgaagct aacaaagacc acgacgtat cacggtcgtg gtctcaaaga    240
acaacaaaca acaaagtccg actgagaagg tgagtggcgg gccctgagct gggggggcggg    300 ggtgttggct ctggaggctg ggtctgagcg taattttgca ccccgcgtc cctgcaggag    360 ccaccatgca gcgggtcaac atgattatgg ctgagagccc tggcctgatc accatctgtc    420
tgctgggcta cctgctgagc gctgagtgca cagtgttttct ggaccatgag aatgccaaca    480 gatcctgaa caggcccaag aggtacaact ctggcaagct ggaagagttt gtgcaggtga    540
gtatctcagg gatccagaca tggggatatg gaggtgcct ctgatcccag ggctcactgt    600
gggtctctct gttcacaggg caacctgaa agggaatgca tggaagagaa gtgcagcttt    660
gaagaggccc gggaagtgtt tgagaacaca gagcggacca cagagttctg gaagcagtat    720
```

```
gtggatgggg accagtgtga aagcaaccc tgtctgaatg gcggcagctg caaggatgac      780
atcaacagct atgagtgctg gtgccccttt ggctttgagg gcaagaactg tgaactggat      840
gtgacctgca acatcaagaa tggccgctgt gaacagttct gcaagaacag cgctgacaac      900
aaggttgtgt gctcctgcac agagggctac agactggctg agaaccagaa agctgtgaa      960 cccgctgtgc cctttccatg cggcagagtg tctgtgtccc agaccagcaa gctgaccaga     1020
gctgaggctg tgttccctga tgtggactat gtgaacagca cagaggctga cacaatcctg     1080
gacaacatca cccagagcac ccagtccttc aatgacttca ccagagttgt tggcggagag     1140
gatgccaagc tggacagtt cccttggcaa gtggtgctga atggcaaagt ggatgccttc     1200
tgcggcggca gcattgtgaa tgagaagtgg attgtgaccg ccgctcactg tgtggaaacc     1260
ggggtcaaga ttacagtggt ggccggggag cacaacattg aggaaacaga gcacacagag     1320
caaaagcgga atgtcatccg gatcatccct caccacaact acaatgccgc catcaacaag     1380
tacaaccatg acattgccct gcttgagctg gatgagcccc tggtcctgaa ctcctatgtg     1440 accctatct gcattgctga caagagtac accaacatct ttctgaagtt tggcagcggc     1500
tatgtgtccg gctggggaag agtgttccac aagggaagat ctgccctggt gctgcagtac     1560
ctgagagtgc cctggtgga tagagccaca tgtctgctga gcaccaagtt caccatctac     1620
aacaacatgt tctgcgccgg cttccatgaa ggcggcagag atagctgtca gggagattct     1680
ggcggccctc atgtgacaga ggtggaaggc accagctttc tgaccggcat catcagctgg     1740
ggagaagagt gtgccatgaa gggcaaatat ggcatctaca ccaaggtgtc ccgctatgtc     1800
aactggatca agaaaagac caagctcacc tgataagcta gctctagatc ataatcagcc     1860
ataccacatt tgtagaggtt ttacttgctt taaaaaacct cccacacctc cccctgaacc     1920
tgaaacataa aatgaatgca attgttgttg ttaacttgtt tattgcagct tataatggtt     1980
acaaataaag caatagcatc acaaatttca caataaagc attttttca ctgcattcta     2040 gttgtggttt gtccaaactc atcaatgtat ctggggaggc tgctggtgaa tattaaccaa     2100
ggtcacccca gttatcggag gagcaaacag gggctaagtc cacacgcgt               2149
```

<210> SEQ ID NO 13
<211> LENGTH: 88
<212> TYPE: DNA
<213> ORGANISM: Artificial Sequence
<220> FEATURE:
<223> OTHER INFORMATION: Intron-1
<220> FEATURE:
<221> NAME/KEY: Intron
<222> LOCATION: (1)..(88)

<400> SEQUENCE: 13

```
gtgagtggcg ggccctgagc tgggggggcgg gggtgttggc tctggaggct gggtctgagc      60
gtaattttgc accccccgcgt ccctgcag                                         88
```

<210> SEQ ID NO 14
<211> LENGTH: 1389
<212> TYPE: DNA
<213> ORGANISM: Artificial Sequence
<220> FEATURE:
<223> OTHER INFORMATION: Codon optimized human factor IX gene-1 without
      artificial intron-2
<220> FEATURE:
<221> NAME/KEY: gene
<222> LOCATION: (1)..(1389)

<400> SEQUENCE: 14

```
atgcagaggg tgaacatgat catggctgag agccctggcc tgatcaccat ctgcctgctg    60
ggctacctgc tgtctgctga gtgcactgtg ttcctggacc atgagaatgc caacaagatc   120
ctgaacaggc ccaagagata caactctggc aagctggagg agtttgtgca gggcaacctg   180
gagagggagt gcatggagga gaagtgcagc tttgaggagg ccagggaggt gtttgagaac   240
actgagagga ccactgagtt ctggaagcag tatgtggatg gggaccagtg tgagagcaac   300
ccctgcctga tgggggcag ctgcaaggat gacatcaaca gctatgagtg ctggtgcccc   360
tttggctttg agggcaagaa ctgtgagctg gatgtgacct gcaacatcaa gaatggcaga   420
tgtgagcagt tctgcaagaa ctctgctgac aacaaggtgg tgtgcagctg cactgagggc   480
tacaggctgg ctgagaacca agagagctgt gagcctgctg tgccattccc atgtggcaga   540
gtgtctgtga gccagaccag caagctgacc agggctgagg ctgtgttccc tgatgtggac   600
tatgtgaaca gcactgaggc tgaaaccatc ctggacaaca tcacccagag cacccagagc   660
ttcaatgact tcaccaggt ggtggggggg gaggatgcca agcctggcca gttcccctgg   720
caagtggtgc tgaatggcaa ggtggatgcc ttctgtgggg gcagcattgt gaatgagaag   780
tggattgtga ctgctgccca ctgtgtggag actggggtga agatcactgt ggtggctggg   840
gagcacaaca ttgaggagac tgagcacact gagcagaaga ggaatgtgat caggatcatc   900
ccccaccaca actacaatgc tgccatcaac aagtacaacc atgacattgc cctgctggag   960
ctggatgagc ccctggtgct gaacagctat gtgacccca tctgcattgc tgacaaggag  1020
tacaccaaca tcttcctgaa gtttggctct ggctatgtgt ctggctgggg cagggtgttc  1080
cacaagggca ggtctgccct ggtgctgcag tacctgaggg tgccccctggt ggacagggcc  1140
acctgcctgc tgagcaccaa gttccacatc tacaacaaca tgttctgtgc tggcttccat  1200
gagggggcag gggacagctg ccagggggac tctggcggcc cccatgtgac tgaggtggag  1260
ggcaccagct tcctgactgg catcatcagc tgggggaggg agtgtgccat gaagggcaag  1320
tatggcatct acaccaaagt ctccagatat gtgaactgga tcaaggagaa gaccaagctg  1380
acctgataa                                                          1389
```

<210> SEQ ID NO 15
<211> LENGTH: 1389
<212> TYPE: DNA
<213> ORGANISM: Artificial Sequence
<220> FEATURE:
<223> OTHER INFORMATION: Codon optimized human factor IX gene-2 without
      artificial intron-2
<220> FEATURE:
<221> NAME/KEY: gene
<222> LOCATION: (1)..(1389)

<400> SEQUENCE: 15

```
atgcagaggg tcaacatgat tatggctgag agccctggcc tgatcaccat ctgtctgctg    60
ggctacctgc tgtctgcaga gtgcacagtg tttctggacc atgagaatgc caacaagatc   120
ctgaacaggc ccaagaggta caactctggc aagctggaag agtttgtgca gggcaacctg   180
gaaagggaat gcatggaaga agagtgcagc tttgagaggg ccaggaagt gtttgagaac   240
acagagagaa ccacagagtt ctggaagcag tatgtggatg gggaccagtg tgaaagcaac   300
ccctgcctga tggtggcag ctgcaaggat gacatcaaca gctatgagtg ctggtgcccc   360
tttggctttg agggcaagaa ctgtgaactg gatgtgacct gcaacatcaa gaatggcaga   420
tgtgaacagt tctgcaagaa ctctgctgac aacaaggttg tgtgctcctg cacagagggc   480
tacagactgg ctgagaacca gaaaagctgt gaacctgctg tgccctttcc atgtggcaga   540
```

```
gtgtctgtgt cccagaccag caagctgacc agagctgagg ctgtgttccc tgatgtggac    600
tatgtgaact ccacagaggc tgagacaatc ctggacaaca tcacccagag cacccagtcc    660
ttcaatgact tcacaagagt tgttggaggg gaagatgcca agcctggaca gttcccttgg    720
caagtggtgc tgaatggcaa agtggatgcc ttctgtggtg gctccattgt gaatgagaag    780
tggattgtga cagctgccca ctgtgtggaa acaggggtca agatcacagt ggtggctggg    840
gagcacaaca ttgaggaaac agagcacaca gagcaaaaga ggaatgtcat caggatcatc    900
cctcaccaca actacaatgc tgccatcaac aagtacaacc atgacattgc cctgcttgag    960
ctggatgagc ccctggtcct gaactcctat gtgacccta tctgcattgc tgacaaagag     1020
tacaccaaca tctttctgaa gtttggctct ggctatgtgt ctggctgggg tagagtgttc    1080
cacaagggaa gatctgccct ggtgctgcag tacctgagag tgcccctggt ggatagagcc    1140
acatgtctgc tgagcaccaa gttcaccatc tacaacaaca tgttctgtgc tgggttccat    1200
gaaggtggca gagactcctg ccagggagat agtggtggcc ctcatgtgac agaggtggaa    1260
ggcaccagct ttctgacagg catcatcagc tggggagaag agtgtgccat gaagggcaaa    1320
tatggcatct acaccaaggt gtccagatat gtcaactgga tcaaagaaaa gaccaagctc    1380
acctgataa                                                            1389

<210> SEQ ID NO 16
<211> LENGTH: 1389
<212> TYPE: DNA
<213> ORGANISM: Artificial Sequence
<220> FEATURE:
<223> OTHER INFORMATION: Codon optimized human factor IX gene-3 without
      artificial intron-2
<220> FEATURE:
<221> NAME/KEY: gene
<222> LOCATION: (1)..(1389)

<400> SEQUENCE: 16
atgcagcggg tcaacatgat tatggctgag agccctggcc tgatcaccat ctgtctgctg     60
ggctacctgc tgagcgctga gtgcacagtg tttctggacc atgagaatgc caacaagatc    120
ctgaacaggc ccaagaggta caactctggc aagctggaag agtttgtgca gggcaacctg    180
gaaagggaat gcatggaaga agagtgcagc tttgagaggc ccggaagtgt gtttgagaac    240
acagagcgga ccacagagtt ctggaagcag tatgtggatg gggaccagtg tgaaagcaac    300
ccctgtctga atggcggcag ctgcaaggat gacatcaaca gctatgagtg ctggtgcccc    360
tttggctttg agggcaagaa ctgtgaactg gatgtgacct gcaacatcaa gaatggccgc    420
tgtgaacagt tctgcaagaa cagcgctgac aacaaggttg tgtgctcctg cacagagggc    480
tacagactgg ctgagaacca gaaaagctgt gaaccegctg tgcccttttcc atgcggcaga    540 gtgtctgtgt cccagaccag caagctgacc agagctgagg ctgtgttccc tgatgtggac    600
tatgtgaaca gcacagaggc tgagacaatc ctggacaaca tcacccagag cacccagtcc    660
ttcaatgact tcaccagagt tgttggcgga gaggatgcca agcctggaca gttcccttgg    720
caagtggtgc tgaatggcaa agtggatgcc ttctgcggcg gcagcattgt gaatgagaag    780
tggattgtga ccgccgctca ctgtgtggaa accggggtca agattacagt ggtggccggg    840
gagcacaaca ttgaggaaac agagcacaca gagcaaaagc ggaatgtcat ccggatcatc    900
cctcaccaca actacaatgc cgccatcaac aagtacaacc atgacattgc cctgcttgag    960
ctggatgagc ccctggtcct gaactcctat gtgacccta tctgcattgc tgacaaagag    1020
```

```
tacaccaaca tctttctgaa gtttggcagc ggctatgtgt ccggctgggg aagagtgttc    1080
cacaagggaa gatctgccct ggtgctgcag tacctgagag tgcccctggt ggatagagcc    1140
acatgtctgc tgagcaccaa gttcaccatc tacaacaaca tgttctgcgc cggcttccat    1200
gaaggcggca gagatagctg tcagggagat tctggcggcc ctcatgtgac agaggtggaa    1260
ggcaccagct ttctgaccgg catcatcagc tggggagaag agtgtgccat gaagggcaaa    1320
tatggcatct acaccaaggt gtcccgctat gtcaactgga tcaaagaaaa gaccaagctc    1380
acctgataa                                                            1389
```

OPTIMIZED HUMAN CLOTTING FACTOR IX GENE EXPRESSION CASSETTES AND THEIR USE

STATEMENT OF PRIORITY

This application is a 35 U.S.C. § 371 national phase application of PCT Application PCT/US2018/035267 filed May 31, 2018, which claims the benefit of U.S. Provisional Patent Application Ser. No. 62/512,833, filed May 31, 2017, the entire contents of each of which are incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 5470-817_ST25.txt, 25,948 bytes in size, generated on Nov. 7, 2019 and filed via EFS-Web, is provided in lieu of a paper copy. This Sequence Listing is hereby incorporated by reference into the specification for its disclosures.

FIELD OF THE INVENTION

The invention relates to synthetic liver-specific promoters and expression constructs for producing polypeptides and functional nucleic acids in the liver of a subject. The invention further relates to optimized polynucleotide sequences encoding Factor IX proteins, vectors comprising the same, and methods of using these compositions to treat a bleeding disorder.

BACKGROUND OF THE INVENTION

Factor IX (FIX) plays a critical role in the coagulation cascade by accelerating the conversion of factor X to factor Xa. Deficiency in FIX activity is responsible for the bleeding disorder hemophilia B. The current treatment for hemophilia B is intravenous infusion of plasma-derived or recombinant FIX protein. Despite this treatment being effective in controlling bleeding episodes, the requirement for frequent infusion, owing to the short half-life of FIX (8-12 hours), makes it inherently costly. Gene therapy has emerged as an attractive strategy for the eventual cure of this disease. However, the progress in delivering a FIX gene using one of the most promising viral vectors, adeno-associated virus (AAV), has suffered due to insufficient levels of expression of FIX.

The present invention overcomes shortcomings in the art by providing a short synthetic liver-specific promoter and expression construct suitable for use in AAV vectors. The invention further provides optimized FIX encoding sequences that are capable of producing supraphysiological levels of FIX for extended periods and methods of their use in treating bleeding disorders.

SUMMARY OF THE INVENTION

The present invention is based in part on the development of a synthetic liver-specific promoter that is less than 200 basepairs in length. The promoter may be used for producing polypeptides and functional nucleic acids in a liver-specific manner, especially using AAV vectors, which have strict length limitations and benefit from the availability of a short but strong promoter.

The present invention is further based in part on the development of optimized FIX encoding sequences that are capable of producing supraphysiological levels of FIX for extended periods.

In one aspect, the present invention relates to a polynucleotide comprising a synthetic liver specific promoter, wherein the promoter comprises the nucleotide sequence of SEQ ID NO: 1 or a sequence at least 90% identical thereto.

In an additional aspect, the present invention relates to a polynucleotide encoding a human Factor IX that has been codon optimized for expression in humans.

In another aspect, the present invention relates to a vector, a cell, and/or a transgenic animal comprising the polynucleotide of the invention.

In a further aspect, the present invention relates to a method of producing a polypeptide or a functional nucleic acid in the liver of a subject, comprising delivering to the subject the polynucleotide, vector, and/or transformed cell of the invention, thereby producing the polypeptide or functional nucleic acid in the liver of the subject.

In an additional aspect, the present invention relates to a method of treating hemophilia B in a subject, comprising delivering to the subject a therapeutically effective amount of the polynucleotide, vector, and/or transformed cell of the invention, thereby treating hemophilia B in the subject.

In another aspect, the present invention relates to a method of increasing the bioavailability of a Factor IX polypeptide in a subject, comprising delivering to the subject an effective amount of the polynucleotide, vector, and/or transformed cell of the invention, thereby increasing the bioavailability of the Factor IX polypeptide in the subject.

In a further aspect, the present invention relates to the use of the polynucleotide, vector, and/or transformed cell of the invention in a method of producing a polypeptide or a functional nucleic acid in the liver of a subject.

In an additional aspect, the present invention relates to the use of the polynucleotide, vector, and/or transformed cell of the invention in a method of treating hemophilia B in a subject.

In another aspect, the present invention relates to the use of the polynucleotide, vector, and/or transformed cell of the invention in a method of increasing the bioavailability of a Factor IX polypeptide in a subject.

In a further aspect, the present invention relates to the use of the polynucleotide, vector, and/or transformed cell of the invention in the preparation of a medicament for producing a polypeptide or a functional nucleic acid in the liver of a subject.

In an additional aspect, the present invention relates to the use of the polynucleotide, vector, and/or transformed cell of the invention in the preparation of a medicament for treating hemophilia B in a subject.

In another aspect, the present invention relates to the use of the polynucleotide, vector, and/or transformed cell of the invention in the preparation of a medicament for increasing the bioavailability of a Factor IX polypeptide in a subject.

These and other aspects of the invention are set forth in more detail in the description of the invention below.

BRIEF DESCRIPTION OF THE DRAWINGS

FIG. 1 shows the structure and sequence of the LXP2.1 promoter (SEQ ID NO: 1). The putative hepatic and housekeeping transcriptional factor binding sites are highlighted by underlining.

FIG. 2 shows the construction of an optimized liver-specific human factor IX (FIX) gene expression cassette.

DETAILED DESCRIPTION OF THE INVENTION

Figure 3:
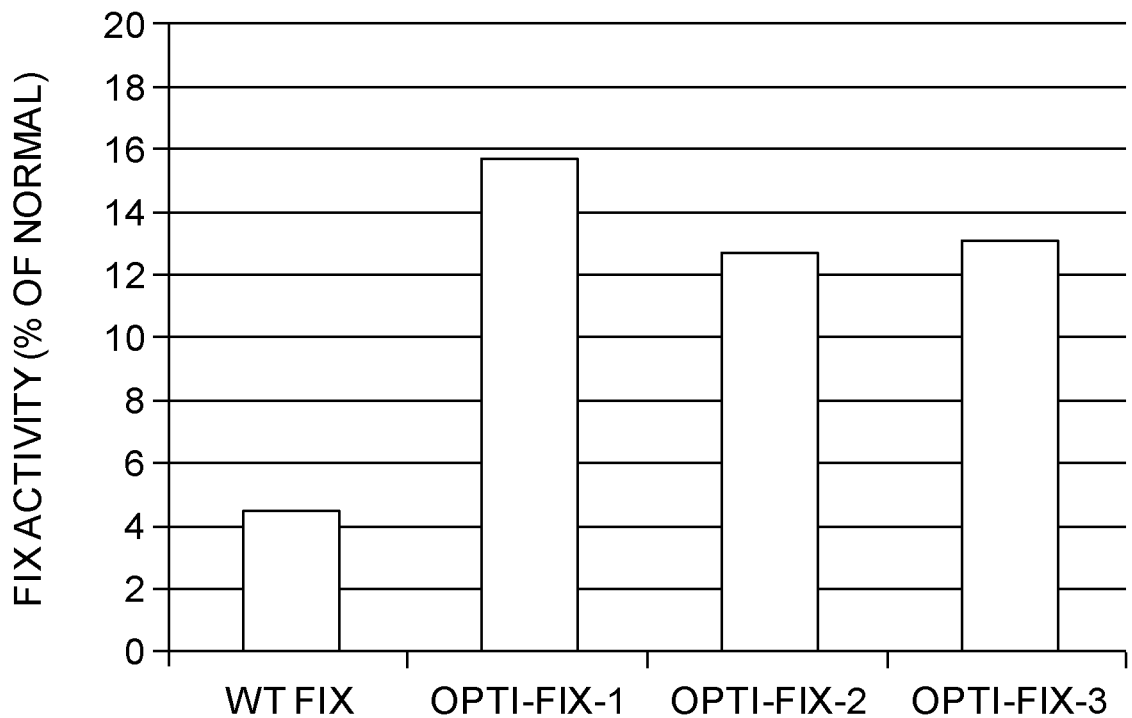
FIG. 3 shows FIX activities in media of Huh7 cells 48 hours after plasmid transfection. Huh7 liver cancer cells were seeded in 6-wells plate and transfected with 2 µg of FIX gene expression constructs. Cell culture media were changed 24 hour later and harvested at 48 hours post transfection in serum-free Opti-MEM medium. FIX activities were measured by APTT test with purified normal FIX protein as a reference standard. Wt FIX gene expression construct contained original human FIX cDNA without codon-optimization but contained the R338L mutation. Opti-FIX-1, 2, 3 gene expression constructs all contained R338L mutation but with different human codon-optimization algorisms as described in the text of EXAMPLE 1.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±10%, ±5%, ±1%, ±0.5%, or even ±0.1% of the specified amount.

The transitional phrase "consisting essentially of" means that the scope of a claim is to be interpreted to encompass the specified materials or steps recited in the claim, and those that do not materially affect the basic and novel characteristic(s) of the claimed invention.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in coagulation-stimulating activity of at least about 50% or more as compared to the activity of a polypeptide consisting of the recited sequence.

The term "enhance" or "increase" or grammatical variations thereof as used herein refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectable activity (at most, an insignificant amount, e.g., less than about 10% or even 5%).

An "effective" amount as used herein is an amount that provides a desired effect.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating a bleeding disorder by the methods of the present invention can be determined by detecting a clinical improvement as indicated by a change in the subject's symptoms and/or clinical parameters as would be well known to one of skill in the art.

By the terms "treat," "treating," or "treatment," it is intended that the severity of the subject's condition is reduced or at least partially improved or modified and that some alleviation, mitigation or decrease in at least one clinical symptom is achieved.

The terms "prevent," "preventing," and "prevention" (and grammatical variations thereof) refer to a decrease or delay in the extent or severity of a disease, disorder and/or clinical symptom(s) after onset relative to what would occur in the absence of carrying out the methods of the invention prior to the onset of the disease, disorder and/or clinical symptom(s). In terms of hemophilia B, "preventing" refers to the occurrence of a lower number and/or severity of bleeding episodes than the number and/or severity of bleeding episodes that occur in the absence of the preventative treatment.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention.

The term "isolated" can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J Biol. Chem.* 267:963 (1992); Wu et al., *J Biol. Chem.* 263:14621 (1988); and Hartmut et al., Canadian Patent Application No. 2,012,311, filed Mar. 15, 1990). In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931). It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., enzymatic activity, protein binding, ligand or receptor binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and enzymatic activity can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV12, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The genomic sequences of various AAV and autonomous parvoviruses, as well as the sequences of the ITRs, Rep proteins, and capsid subunits are known in the art. Such sequences may be found in the literature or in public databases such as the GenBank® database. See, e.g., GenBank® Accession Numbers NC 002077, NC 001401, NC 001729, NC 001863, NC 001829, NC 001862, NC 000883, NC 001701, NC 001510, AF063497, U89790, AF043303, AF028705, AF028704, J02275, J01901, J02275, X01457, AF288061, AH009962, AY028226, AY028223, NC 001358, NC 001540, AF513851, AF513852, AY530579, AY631965, AY631966; the disclosures of which are incorporated herein in their entirety. See also, e.g., Srivistava et al., (1983) *J. Virol.* 45:555; Chiorini et al., (1998) *J. Virol.* 71:6823; Chiorini et al., (1999) *J. Virol.* 73:1309; Bantel-Schaal et al., (1999) *J Virol.* 73:939; Xiao et al., (1999) *J. Virol.* 73:3994; Muramatsu et al., (1996) *Virology* 221:208; Shade et al., (1986) *J Virol.* 58:921; Gao et al., (2002) *Proc. Nat. Acad. Sci. USA* 99:11854; international patent publications WO 00/28061, WO 99/61601, WO 98/11244; U.S. Pat. No. 6,156,303; the disclosures of which are incorporated herein in their entirety. See also Table 1. An early description of the AAV1, AAV2 and AAV3 terminal repeat sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) *Curr. Topics Microbiol. Immunol.* 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11, or 12 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617, AAR26465 |
| AAV11 | AAT46339, AY631966 |
| AAV12 | ABI16639, DQ813647 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |

TABLE 1-continued

| | GenBank Accession Number |
|---|---|
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |

TABLE 1-continued

| | GenBank Accession Number |
|---|---|
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

TABLE 2

| Amino Acid Residue | Three-Letter Code | One-Letter Code |
|---|---|---|
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfation).

TABLE 3

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) *Annu. Rev. Biophys. Biomol. Struct.* 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/

68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The terms "rAAV particle" and "rAAV virion" are used interchangeably here. A "rAAV particle" or "rAAV virion" comprises a rAAV vector genome packaged within an AAV capsid.

The AAV capsid structure is described in more detail in BERNARD N. FIELDS et al., VIROLOGY, volume 2, chapters 69 & 70 (4th ed., Lippincott-Raven Publishers).

The term "pharmacokinetic properties" has its usual and customary meaning and refers to the absorption, distribution, metabolism and excretion of the FIX protein.

The usual and customary meaning of "bioavailability" is the fraction or amount of an administered dose of a biologically active drug that reaches the systemic circulation. In the context of embodiments of the present invention, the term "bioavailability" includes the usual and customary meaning but, in addition, is taken to have a broader meaning to include the extent to which the FIX protein is bioactive. In the case of FIX, for example, one measurement of "bioavailability" is the procoagulant activity of FIX protein obtained in the circulation post-infusion.

"Posttranslational modification" has its usual and customary meaning and includes but is not limited to removal of leader sequence, γ-carboxylation of glutamic acid residues, β-hydroxylation of aspartic acid residues, N-linked glycosylation of asparagine residues, O-linked glycosylation of serine and/or threonine residues, sulfation of tyrosine residues, phosphorylation of serine residues and any combination thereof.

As used herein, "biological activity" is determined with reference to a standard derived, e.g., from human plasma, or recombinantly produced. For FIX, the standard can be BENEFIX® (Pfizer) or MONONINE® (CSL Behring). The biological activity of the standard is taken to be 100%.

The term "Factor IX protein" or "FIX protein" as used herein includes wild type FIX protein as well as naturally occurring or man-made proteins. A FIX protein of this invention can further include mutated forms of FIX as are known in the literature (e.g., the Padua mutation). A FIX protein of this invention further includes any other naturally occurring human FIX protein or manmade human FIX protein now known or later identified, and derivatives and active fragments/active domains thereof, as are known in the art.

The amino acid sequence of FIX from multiple mammalian species is available from sequence databases such as GenBank. Examples of FIX sequences are found in the table below.

| Species | GenBank Accession No. |
| --- | --- |
| Homo sapiens | AAB59620.1 |
| Felis catus | AAR26346.1 |
| Mus musculus | NP_032005.1 |
| Sus scrofa | NP_001157475.1 |
| Canis lupus familiaris | AAA75006.1 |
| Rattus norvegicus | NP_113728.1 |
| Macaca mulatta | NP_001103153.1 |

A FIX protein of this invention further includes the pharmacologically active form of FIX, which is the molecule from which the signal peptide has been removed and the protein has been cleaved by the action of proteases (or by engineering it out of the protein by removing it at the nucleic acid level), resulting in two non-contiguous polypeptide chains that are linked by a disulfide bridge.

The amino acid sequence of human FIX protein is well-known in the art and can be found, for example in GenBank Accession No. AAB59620.1. The human FIX protein is 461 amino acids in length and is comprised of a signal peptide (residues 1-46), a Gla domain (residues 28-92), EGF domains (residues 93-129), and a trypsin domain (residues 226-454).

The term "half-life" is a broad term which includes the usual and customary meaning as well as the usual and customary meaning found in the scientific literature for FIX. Specifically included in this definition is a measurement of a parameter associated with FIX which defines the time post-infusion for a decrease from an initial value measured at infusion to half the initial value. In some embodiments, the half-life of FIX can be measured in blood and/or blood components using an antibody to FIX in a variety of immunoassays, as are well known in the art and as described herein. Alternatively, half-life may be measured as a decrease in FIX activity using functional assays including standard clotting assays, as are well known in the art and as described herein.

The term "recovery" as used herein includes the amount of FIX, as measured by any acceptable method including but not limited to FIX antigen levels or FIX protease or clotting activity levels, detected in a recipient animal or human subject (e.g., in the circulation) at the earliest practical time of removing a biological sample (e.g., a blood or blood product sample) for the purpose of measuring the level of FIX following its infusion, injection, delivery or administration otherwise. With current methodologies, the earliest biological sampling time for measuring FIX recovery typically falls within the first 15 minutes post infusion, injection, or delivery/administration otherwise of the FIX, but it is reasonable to expect quicker sampling times as scientific and/or clinical technologies improve. In essence, the recovery value for FIX is meant here to represent the maximum fraction of infused, injected or otherwise delivered/administered FIX that can be measured in the recipient (e.g., in the circulation) at the earliest possible time point following infusion, injection, or other delivery to a recipient animal or patient.

As used herein, a "transformed" cell is a cell that has been transformed, transduced and/or transfected with a nucleic acid molecule encoding a FIX protein of this invention, including but not limited to a FIX protein vector constructed using recombinant DNA techniques.

As used herein, the term "bleeding disorder" reflects any defect, congenital, acquired, or induced, of cellular, physiological, or molecular origin that is manifested in bleedings. Examples are clotting factor deficiencies (e.g., hemophilia A and B or deficiency of coagulation Factors XI, VII, VIII, or IX), clotting factor inhibitors, defective platelet function, thrombocytopenia, von Willebrand's disease, or bleeding induced by surgery or trauma.

Excessive bleedings also occur in subjects with a normally functioning blood clotting cascade (no clotting factor deficiencies or inhibitors against any of the coagulation factors) and may be caused by a defective platelet function, thrombocytopenia or von Willebrand's disease. In such cases, the bleedings may be likened to those bleedings caused by hemophilia because the haemostatic system, as in hemophilia, lacks or has abnormal essential clotting "compounds" (such as platelets or von Willebrand factor protein), causing major bleedings. In subjects who experience extensive tissue damage in association with surgery or trauma, the normal haemostatic mechanism may be overwhelmed by the demand of immediate hemostasis and they may develop bleeding in spite of a normal haemostatic mechanism. Achieving satisfactory hemostasis also is a problem when bleedings occur in organs such as the brain, inner ear region and eyes, with limited possibility for surgical hemostasis. The same problem may arise in the process of taking biopsies from various organs (liver, lung, tumor tissue, gastrointestinal tract) as well as in laparoscopic surgery. Common for all these situations is the difficulty to provide hemostasis by surgical techniques (sutures, clips, etc.), which also is the case when bleeding is diffuse (hemorrhagic gastritis and profuse uterine bleeding). Acute and profuse bleedings may also occur in subjects on anticoagulant therapy in whom a defective hemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical hemostasis, and which may result in diffuse bleeding from a large area. Also, intracerebral hemorrhage is the least treatable form of stroke and is associated with high mortality and hematoma growth in the first few hours following intracerebral hemorrhage. Another situation that may cause problems in the case of unsatisfactory hemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with hemophilia. In another embodiment, the bleeding is associated with hemophilia with acquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with hemorrhagic gastritis. In another embodiment, the bleeding is profuse uterine bleeding. In another embodiment, the bleeding is occurring in organs with a limited possibility for mechanical hemostasis. In another embodiment, the bleeding is occurring in the brain, inner ear region or eyes. In another embodiment, the bleeding is associated with the process of taking biopsies. In another embodiment, the bleeding is associated with anticoagulant therapy.

A "subject" of the invention includes any animal having or susceptible to a bleeding disorder or bleeding condition for which control of bleeding is needed and/or desired, which can be treated, ameliorated or prevented by administration of FIX to the subject, (such as hemophilia B and acquired FIX deficiency (e.g., due to autoantibodies directed against FIX or hematological malignancy)). Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of a bleeding disorder or bleeding condition for which control is needed and/or desired. Alternatively, a subject according to the invention can also include a subject not previously known or suspected to be at risk of a bleeding disorder or bleeding condition for which control is needed or desired. As a further option, the subject can be a laboratory animal and/or an animal model of disease.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

Promoters and Expression Cassettes

One aspect of the present invention relates to a polynucleotide comprising a synthetic liver specific promoter, wherein the promoter comprises, consists essentially of, or consists of the nucleotide sequence of SEQ ID NO: 1 or a sequence at least about 90% identical thereto. In some embodiments, the nucleotide sequence is at least about 90%, 91%, 92%, 93%, 94%, 95%, 96%, 97%, 98%, or 99% identical to the nucleotide sequence of SEQ ID NO: 1. The promoter is a short (less than 200 basepairs) and strong liver-specific promoter that is ideal for liver specific expression of a polynucleotide of interest and is especially suited for use in AAV vectors due to its short length and the limited capacity of AAV vectors. The promoter was designed to contain a conserved basal promoter element and transcription initiation site. The basal promoter is linked at its 5' end with a number of liver-specific transcriptional factor binding sites for liver-specific expression (FIG. 1). The promoter exhibits high activity as initially identified in vitro using a luciferase reporter gene and transfection experiments in human liver cancer cell line Huh7 and then confirmed in vivo in mice.

The promoter may be operably linked to a polynucleotide of interest. In some embodiments, the polynucleotide of interest encodes a polypeptide or a functional nucleic acid. In certain embodiments, the polynucleotide of interest encodes a clotting factor, e.g., FVIX. In some embodiments, the polynucleotide sequence encoding FIX has been codon optimized for expression in humans. In certain embodiments, the codon-optimized sequence comprises, consists essentially of, or consists of a sequence that is at least 90% identical to one of SEQ ID NOS: 14-16, e.g., at least about 90%, 91%, 92%, 93%, 94%, 95%, 96%, 97%, 98%, or 99% identical to the nucleotide sequence of SEQ ID NOS: 14-16. In some embodiments, the polynucleotide sequence encoding FIX encodes a FIX sequence comprising a mutation or sequence alteration known in the art. In one example, the Factor IX encoding sequence comprises a missense mutation resulting in a R338L mutation (the Padua mutation) or other mutation at that site (numbering with respect to human Factor IX).

In some embodiments, the polynucleotide further comprises a synthetic 5'-untranslated region (5'-UTR) between the promoter and the polynucleotide of interest. The synthetic 5'-UTR may comprise, consist essentially of, or consist of the nucleotide sequence of SEQ ID NO: 3 or a sequence at least about 90% identical thereto, e.g., at least about 90%, 91%, 92%, 93%, 94%, 95%, 96%, 97%, 98%, or 99% identical to the nucleotide sequence of SEQ ID NO: 3. In some embodiments, the synthetic 5'-UTR comprises a synthetic intron. The synthetic intron may comprise, consist essentially of, or consist of the nucleotide sequence of SEQ ID NO: 13 or a sequence at least about 90% identical thereto, e.g., at least about 90%, 91%, 92%, 93%, 94%, 95%, 96%, 97%, 98%, or 99% identical to the nucleotide sequence of SEQ ID NO: 13. In some embodiments, the synthetic 5'-UTR and synthetic intron comprise, consist essentially of, or consist of the nucleotide sequence of SEQ ID NO: 4 or a sequence at least about 90% identical thereto, e.g., at least about 90%, 91%, 92%, 93%, 94%, 95%, 96%, 97%, 98%, or 99% identical to the nucleotide sequence of SEQ ID NO: 4. In certain embodiments, the promoter, synthetic 5'-UTR and synthetic intron comprise, consist essentially of, or consist of the nucleotide sequence of SEQ ID NO: 2 or a sequence at least about 90% identical thereto, e.g., at least about 90%, 91%, 92%, 93%, 94%, 95%, 96%, 97%, 98%, or 99% identical to the nucleotide sequence of SEQ ID NO: 2.

In some embodiments, the polynucleotide of interest linked to the promoter of the invention or to any promoter comprises a synthetic intron. In some embodiments, the synthetic intron comprises, consists essentially of, or consists of the nucleotide sequence of SEQ ID NO: 5 or a sequence at least about 90% identical thereto, e.g., at least about 90%, 91%, 92%, 93%, 94%, 95%, 96%, 97%, 98%, or 99% identical to the nucleotide sequence of SEQ ID NO: 5.

In certain embodiments, the polynucleotide of interest is a codon-optimized Factor IX encoding sequence and the codon-optimized Factor IX encoding sequence and synthetic intron together comprise, consist essentially of, or consist of the nucleotide sequence of one of SEQ ID NOS: 6, 7, or 8 or a sequence at least about 90% identical thereto, e.g., at least about 90%, 91%, 92%, 93%, 94%, 95%, 96%, 97%, 98%, or 99% identical to the nucleotide sequence of SEQ ID NOS: 6, 7, or 8.

In certain embodiments, any of the polynucleotides of the invention may be operably linked to a polyadenylation site, e.g., a bidirectional polyadenylation site. In some embodiments, the polyadenylation site comprises, consists essentially of, or consists of the nucleotide sequence of SEQ ID NO: 9 or a sequence at least about 90% identical thereto, e.g., at least about 90%, 91%, 92%, 93%, 94%, 95%, 96%, 97%, 98%, or 99% identical to the nucleotide sequence of SEQ ID NO: 9.

Another aspect of the invention relates to a polynucleotide encoding a human Factor IX that has been codon optimized for expression in humans. In certain embodiments, the codon-optimized sequence comprises, consists essentially of, or consists of a sequence that is at least 90% identical to one of SEQ ID NOS: 14-16, e.g., at least about 90%, 91%, 92%, 93%, 94%, 95%, 96%, 97%, 98%, or 99% identical to the nucleotide sequence of SEQ ID NOS: 14-16. In some embodiments, the codon-optimized sequence comprises a synthetic intron. In some embodiments, the synthetic intron comprises, consists essentially of, or consists of the nucleotide sequence of SEQ ID NO: 5 or a sequence at least about 90% identical thereto, e.g., at least about 90%, 91%, 92%, 93%, 94%, 95%, 96%, 97%, 98%, or 99% identical to the nucleotide sequence of SEQ ID NO: 5. In certain embodiments, the codon-optimized Factor IX encoding sequence and synthetic intron together comprise, consist essentially of, or consist of the nucleotide sequence of one of SEQ ID NOS: 6, 7, or 8 or a sequence at least about 90% identical thereto, e.g., at least about 90%, 91%, 92%, 93%, 94%, 95%, 96%, 97%, 98%, or 99% identical to the nucleotide sequence of SEQ ID NOS: 6, 7, or 8.

In certain embodiments, any of the polynucleotides of the invention may be in the form of an expression cassette, e.g., a cassette compressing a promoter, a 5'UTR, a polynucleotide of interest, one or more synthetic introns, and/or a polyadenylation site, in any combination and in any order. In some embodiments, the expression cassette comprises, consists essentially of, or consists of the nucleotide sequence of one of SEQ ID NOS: 10, 11, or 12 or a sequence at least about 90% identical thereto, e.g., at least about 90%, 91%, 92%, 93%, 94%, 95%, 96%, 97%, 98%, or 99% identical to the nucleotide sequence of SEQ ID NOS: 10, 11, or 12.

Another aspect of the invention is a vector, e.g., an expression vector, comprising the polynucleotide of the invention. The vector may be any type of vector known in the art, including, without limitation, plasmid vectors and viral vectors. In some embodiments, the viral vector is a retroviral or lentiviral vector. In some embodiments, the viral vector is an AAV vector from any known AAV serotype including without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, avian AAV, bovine AAV, canine AAV, equine AAV, and ovine AAV and any other AAV now known or later discovered. In some embodiments, the AAV vector is AAV8 or AAV9.

A further aspect of the invention relates to a cell comprising the polynucleotide and/or vector of the invention (e.g., an isolated cell, a transformed cell, a recombinant cell, an in vitro or ex vivo cell, etc.). Thus, various embodiments of the invention are directed to recombinant host cells containing the vector (e.g., expression cassette). Such a cell can be isolated and/or present in a transgenic animal. Transformation of cells is described further below.

Another aspect of the invention relates to a transgenic non-human animal comprising the polynucleotide, vector, and/or transformed cell of the invention. Transgenic animals are described further below.

The polynucleotide, vector, and/or cell of this invention can be included in a pharmaceutical composition. Some embodiments are directed to a kit which includes the polynucleotide, vector, and/or cell of this invention and/or reagents and/or instructions for using the kit, e.g., to carry out the methods of this invention.

Methods of the Invention

A further aspect of the invention relates to the use of the promoters, optimized sequences, and expression cassettes of the invention to produce a polypeptide or a functional nucleic acid, e.g., in a liver-specific manner. Thus, one aspect relates to a method of producing a polypeptide or a functional nucleic acid in the liver of a subject, comprising delivering to the subject the polynucleotide, vector, and/or transformed cell of the invention, thereby producing the polypeptide or functional nucleic acid in the liver of the subject. The polynucleotide, vector, and/or transformed cell are delivered under conditions whereby expression of the polynucleotide of interest occurs to produce a polypeptide or functional nucleic acid. Such conditions are well known in the art and described further below.

Another aspect of the invention relates to a method of treating hemophilia B or acquired factor IX deficiency in a subject using the promoters, optimized sequences, and expression cassettes of the invention, comprising delivering to the subject a therapeutically effective amount of the polynucleotide, vector, and/or transformed cell of the invention, thereby treating hemophilia B or acquired factor IX deficiency in the subject. In some embodiments, the polynucleotide of interest encodes a FIX polypeptide as described above.

A further aspect of the invention relates to a method of increasing the bioavailability of a FIX polypeptide in a subject using the promoters, optimized sequences, and expression cassettes of the invention, comprising delivering to the subject an effective amount of the polynucleotide, vector, and/or transformed cell of the invention, thereby increasing the bioavailability of the FIX polypeptide in the subject. In this aspect, the polynucleotide of interest may encode a FIX polypeptide as described above.

One aspect of the invention relates to a method of producing FIX in the liver of a subject, comprising delivering to the subject the polynucleotide encoding the FIX polypeptide, vector, and/or transformed cell of the invention, thereby producing FIX in the liver of the subject.

A further aspect of the invention relates to a method of increasing the bioavailability of a FIX polypeptide in a subject, comprising delivering to the subject an effective amount of the polynucleotide encoding the FIX polypeptide, vector, and/or transformed cell of the invention, thereby increasing the bioavailability of FIX polypeptide in the subject.

Bleeding disorders that can be treated according to the methods of this invention include any disorder that can be treated with FIX, such as hemophilia B and acquired FIX deficiency. Such treatment protocols and dosing regimens for administering or delivering a polynucleotide encoding a FIX protein of this invention to a subject (e.g., a subject in need thereof) are well known in the art.

In embodiments of the invention, the dosage of a vector (e.g., a viral vector or other nucleic acid vector) encoding the FIX protein of this invention can be in an amount such that a therapeutic plasma concentration of FIX protein is achieved. A therapeutic concentration of FIX protein is considered to be above 1% of the normal level of healthy individuals, which is measured on the average 100%, thus, one international unit (IU) of FIX in 1 mL of normal human plasma. One of skill in the art would be able to determine the optimal dose for a given subject and a given condition.

For treatment in connection with deliberate interventions, the FIX protein of the invention will typically be administered within about 24 hours prior to performing the intervention, and for as much as 7 days or more thereafter. Administration as a coagulant can be by a variety of routes as described herein.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. Alternatively, the pharmaceutical compositions may be formulated for administration in various ways, including, but not limited to, orally, subcutaneously, intravenously, intracerebrally, intranasally, transdermally, intraperitoneally, intramuscularly, intrapulmonary, vaginally, rectally, intraocularly, or in any other acceptable manner.

The compositions for parenteral administration comprise polynucleotides encoding the FIX protein, vectors, or cells of the invention in combination with (e.g., dissolved in), a pharmaceutically acceptable carrier, preferably an aqueous carrier. A variety of aqueous carriers may be used, such as water, buffered water, 0.4% saline, 0.3% glycine and the like. The polynucleotides encoding the FIX protein, vectors, or cells of the invention may also be formulated with compositions that prolong stability and storage, such as methionine and sucrose. The polynucleotides encoding the FIX protein, vectors, or cells of the invention can also be formulated into liposome preparations for delivery or targeting to the site(s) of injury. Liposome preparations are generally described in, e.g., U.S. Pat. Nos. 4,837,028, 4,501,728, and 4,975,282. The compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The compositions may also contain preservatives, isotonifiers, non-ionic surfactants or detergents, antioxidants and/or other miscellaneous additives.

The concentration of the polynucleotides encoding the FIX protein, vectors or cells in these formulations can vary widely, i.e., from less than about 0.5% by weight, usually at or at least about 1% by weight to as much as about 15 or 20% by weight and will be selected primarily by fluid volumes, viscosities, etc., in accordance with the particular mode of administration selected. Actual methods for preparing parenterally administrable compositions will be known or apparent to those skilled in the art and are described in more detail in, for example, *Remington's Pharmaceutical Sciences*, 21$^{st}$ ed., Mack Publishing Company, Easton, Pa. (2005).

The compositions comprising the nucleic acid molecules that encode the FIX protein, vectors, or cells of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as a "therapeutically effective amount." As will be understood by the person skilled in the art amounts effective for this purpose will depend on the severity of the disease or injury as well as the weight and general state of the subject.

In prophylactic applications, compositions containing the polynucleotides encoding the FIX protein, vectors or cells of the invention are administered to a subject susceptible to or otherwise at risk of a disease state or injury to enhance the subject's own coagulative capability. Such an amount is defined to be a "prophylactically effective dose." In prophylactic applications, the precise amounts once again depend on the subject's state of health and weight.

Single or multiple administrations of the compositions can be carried out with dose levels and patterns being selected by the treating physician. For ambulatory subjects requiring daily maintenance levels, the polynucleotides encoding the FIX protein, vectors or cells may be administered by continuous infusion using e.g., a portable pump system.

The polynucleotides encoding the FIX protein, vectors or cells of the present invention may also be formulated in sustained, or extended release formulations. Methods of formulating sustained or extended release compositions are known in the art and include, but are not limited to, semi-permeable matrices of solid hydrophobic particles containing the polynucleotides, vectors or cells.

Local delivery of the polynucleotides encoding the FIX protein, vectors or cells of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of FIX protein sufficient to effectively treat the subject.

In some embodiments, the polynucleotide of interest (e.g., a FIX protein) is delivered to the subject using an AAV vector. Thus, the invention also provides AAV virus particles (i.e., virions) comprising the polynucleotide of interest, wherein the virus particle packages (i.e., encapsidates) a vector genome, optionally an AAV vector genome.

In particular embodiments, the virion is a recombinant vector comprising a heterologous polynucleotide of interest, e.g., for delivery to a cell. Thus, the present invention is useful for the delivery of polynucleotides to cells in vitro, ex vivo, and in vivo. In representative embodiments, the recombinant vector of the invention can be advantageously employed to deliver or transfer polynucleotides to animal (e.g., mammalian) cells, e.g., to liver cells when using the liver-specific promoter of the invention.

Any heterologous nucleotide sequence(s) may be delivered by a virus vector of the present invention. Polynucleotides of interest include polynucleotides encoding polypeptides, optionally therapeutic (e.g., for medical or veterinary uses) and/or immunogenic (e.g., for vaccines) polypeptides.

Therapeutic polypeptides include, but are not limited to, cystic fibrosis transmembrane regulator protein (CFTR), dystrophin (including the protein product of dystrophin mini-genes or micro-genes, see, e.g., Vincent et al., (1993) *Nature Genetics* 5:130; U.S. Patent Publication No. 2003017131; Wang et al., (2000) *Proc. Natl. Acad. Sci. USA* 97:13714-9 [mini-dystrophin]; Harper et al., (2002) *Nature Med.* 8:253-61 [micro-dystrophin]); mini-agrin, a laminin-α2, a sarcoglycan (α, β, γ or δ), Fukutin-related protein, myostatin pro-peptide, follistatin, dominant negative myostatin, an angiogenic factor (e.g., VEGF, angiopoietin-1 or 2), an anti-apoptotic factor (e.g., heme-oxygenase-1, TGF-β, inhibitors of pro-apoptotic signals such as caspases, proteases, kinases, death receptors [e.g., CD-095], modulators of cytochrome C release, inhibitors of mitochondrial pore opening and swelling); activin type II soluble receptor, anti-inflammatory polypeptides such as the Ikappa B dominant mutant, sarcospan, utrophin, mini-utrophin, antibodies or antibody fragments against myostatin or myostatin propeptide, cell cycle modulators, Rho kinase modulators such as Cethrin, which is a modified bacterial C3 exoenzyme [available from BioAxone Therapeutics, Inc., Saint-Lauren, Quebec, Canada], BCL-xL, BCL2, XIAP, FLICEc-s, dominant-negative caspase-8, dominant negative caspase-9, SPI-6 (see, e.g., U.S. Patent Application No. 20070026076), transcriptional factor PGC-α1, Pinch gene, ILK gene and thymosin (β4 gene), clotting factors (e.g., Factor VIII, Factor IX, Factor X, etc.), erythropoietin, angiostatin, endostatin, catalase, tyrosine hydroxylase, an intracellular and/or extracellular superoxide dismutase, leptin, the LDL receptor, neprilysin, lipoprotein lipase, ornithine transcarbamylase, β-globin, α-globin, spectrin, α$_1$-antitrypsin, methyl cytosine binding protein 2, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, a cytokine (e.g., α-interferon, β-interferon, interferon-γ, interleukins-1 through -14, granulocyte-macrophage colony stimulating factor, lymphotoxin, and the like), peptide growth factors, neurotrophic factors and hormones (e.g., somatotropin, insulin, insulin-like growth factors including IGF-1 and IGF-2, GLP-1, platelet derived growth factor, epidermal growth factor, fibroblast growth factor, nerve growth factor, neurotrophic factor-3 and -4, brain-derived neurotrophic factor, glial derived growth factor, transforming growth factor-α and -β, and the like), bone morphogenic proteins (including RANKL and VEGF), a lysosomal protein, a glutamate receptor, a lymphokine, soluble CD4, an Fc receptor, a T cell receptor, ApoE, ApoC, inhibitor 1 of protein phosphatase inhibitor 1 (I-1), phospholamban, serca2a, lysosomal acid α-glucosidase, α-galactosidase A, Barkct, β2-adrenergic receptor, β2-adrenergic receptor kinase (BARK), phosphoinositide-3 kinase (PI3 kinase), calsarcin, a receptor (e.g., the tumor necrosis growth factor-α soluble receptor), an anti-inflammatory factor such as IRAP, Pim-1, PGC-1α, SOD-1, SOD-2, ECF-SOD, kallikrein, thymosin-β4, hypoxia-inducible transcription factor [HIF], an angiogenic factor, S100A1, parvalbumin, adenylyl cyclase type 6, a molecule that effects G-protein coupled receptor kinase type 2 knockdown such as a truncated constitutively active bARKct; phospholamban inhibitory or dominant-negative molecules such as phospholamban S16E, a monoclonal antibody (including single chain monoclonal antibodies) or a suicide gene product (e.g., thymidine kinase, cytosine deaminase, diphtheria toxin, and tumor necrosis factors such as TNF-α), and any other polypeptide that has a therapeutic effect in a subject in need thereof.

Heterologous nucleotide sequences encoding polypeptides include those encoding reporter polypeptides (e.g., an enzyme). Reporter polypeptides are known in the art and include, but are not limited to, a fluorescent protein (e.g., EGFP, GFP, RFP, BFP, YFP, or dsRED2), an enzyme that produces a detectable product, such as luciferase (e.g., from *Gaussia, Renilla*, or *Photinus*), β-galactosidase, β-glucuronidase, alkaline phosphatase, and chloramphenicol acetyltransferase gene, or proteins that can be directly detected. Virtually any protein can be directly detected by using, for example, specific antibodies to the protein. Additional markers (and associated antibiotics) that are suitable for either positive or negative selection of eukaryotic cells are disclosed in Sambrook and Russell (2001), *Molecular Cloning*, 3rd Ed., Cold Spring Harbor Laboratory Press, Cold Spring Harbor, N.Y., and Ausubel et al. (1992), *Current Protocols in Molecular Biology*, John Wiley & Sons, including periodic updates.

Alternatively, the heterologous nucleic acid may encode a functional RNA, e.g., an antisense oligonucleotide, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including small interfering RNAs (siRNA) that mediate gene silencing (see, Sharp et al., (2000) *Science* 287:2431), microRNA, or other non-translated "functional" RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi or antisense RNA against the multiple drug resistance (MDR) gene product (e.g., to treat tumors and/or for administration to the heart to prevent damage by chemotherapy), RNAi or antisense RNA against myostatin (Duchenne or Becker muscular dystrophy), RNAi or antisense RNA against VEGF or a tumor immunogen including but not limited to those tumor immunogens specifically described herein (to treat tumors), RNAi or antisense oligonucleotides targeting mutated dystrophins (Duchenne or Becker muscular dystrophy), RNAi or antisense RNA against the hepatitis B surface antigen gene (to prevent and/or treat hepatitis B infection), RNAi or antisense RNA against the HIV tat and/or rev genes (to prevent and/or treat HIV) and/or RNAi or antisense RNA against any other immunogen from a pathogen (to protect a subject from the pathogen) or a defective gene product (to prevent or treat disease). RNAi or antisense RNA against the targets described above or any other target can also be employed as a research reagent.

As is known in the art, anti-sense nucleic acids (e.g., DNA or RNA) and inhibitory RNA (e.g., microRNA and RNAi such as siRNA or shRNA) sequences can be used to induce "exon skipping" in patients with muscular dystrophy arising from defects in the dystrophin gene. Thus, the heterologous nucleic acid can encode an antisense nucleic acid or inhibitory RNA that induces appropriate exon skipping. Those skilled in the art will appreciate that the particular approach to exon skipping depends upon the nature of the underlying defect in the dystrophin gene, and numerous such strategies are known in the art. Exemplary antisense nucleic acids and inhibitory RNA sequences target the upstream branch point and/or downstream donor splice site and/or internal splicing enhancer sequence of one or more of the dystrophin exons (e.g., exons 19 or 23). For example, in particular embodiments, the heterologous nucleic acid encodes an antisense nucleic acid or inhibitory RNA directed against the upstream branch point and downstream splice donor site of exon 19 or 23 of the dystrophin gene. Such sequences can be incorporated into an AAV vector delivering a modified U7 snRNA and the antisense nucleic acid or inhibitory RNA (see, e.g., Goyenvalle et al., (2004) *Science* 306:1796-1799). As another strategy, a modified U1 snRNA can be incorporated into an AAV vector along with siRNA, microRNA or antisense RNA complementary to the upstream and downstream splice sites of a dystrophin exon (e.g., exon 19 or 23) (see, e.g., Denti et al., (2006) *Proc. Nat. Acad. Sci. USA* 103: 3758-3763). Further, antisense nucleic acids and inhibitory RNA can target the splicing enhancer sequences within exons 19, 43, 45 or 53 (see, e.g., U.S. Pat. Nos. 6,653,467; 6,727,355; and 6,653,466).

Ribozymes are RNA-protein complexes that cleave nucleic acids in a site-specific fashion. Ribozymes have specific catalytic domains that possess endonuclease activity (Kim et al., (1987) *Proc. Natl. Acad. Sci. USA* 84:8788; Gerlach et al., (1987) *Nature* 328:802; Forster and Symons, (1987) *Cell* 49:211). For example, a large number of ribozymes accelerate phosphoester transfer reactions with a high degree of specificity, often cleaving only one of several phosphoesters in an oligonucleotide substrate (Michel and Westhof, (1990) *J. Mol. Biol.* 216:585; Reinhold-Hurek and Shub, (1992) *Nature* 357:173). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, (1989) *Nature* 338:217). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of nucleic acid expression may be particularly suited to therapeutic applications (Scanlon et al., (1991) *Proc. Natl. Acad. Sci. USA* 88:10591; Sarver et al., (1990) *Science* 247:1222; Sioud et al., (1992)*J. Mol. Biol.* 223:831).

MicroRNAs (mir) are natural cellular RNA molecules that can regulate the expression of multiple genes by controlling the stability of the mRNA. Over-expression or diminution of a particular microRNA can be used to treat a dysfunction and has been shown to be effective in a number of disease states and animal models of disease (see, e.g., Couzin, (2008) *Science* 319:1782-4). The chimeric AAV can be used to deliver microRNA into cells, tissues and subjects for the treatment of genetic and acquired diseases, or to enhance functionality and promote growth of certain tissues. For example, mir-1, mir-133, mir-206 and/or mir-208 can be used to treat cardiac and skeletal muscle disease (see, e.g., Chen et al., (2006) *Genet.* 38:228-33; van Rooij et al., (2008) *Trends Genet.* 24:159-66). MicroRNA can also be used to modulate the immune system after gene delivery (Brown et al., (2007) *Blood* 110:4144-52).

The term "antisense oligonucleotide" (including "antisense RNA") as used herein, refers to a nucleic acid that is complementary to and specifically hybridizes to a specified DNA or RNA sequence. Antisense oligonucleotides and nucleic acids that encode the same can be made in accordance with conventional techniques. See, e.g., U.S. Pat. No. 5,023,243 to Tullis; U.S. Pat. No. 5,149,797 to Pederson et al.

Those skilled in the art will appreciate that it is not necessary that the antisense oligonucleotide be fully complementary to the target sequence as long as the degree of sequence similarity is sufficient for the antisense nucleotide sequence to specifically hybridize to its target (as defined above) and reduce production of the protein product (e.g., by at least about 30%, 40%, 50%, 60%, 70%, 80%, 90%, 95% or more).

To determine the specificity of hybridization, hybridization of such oligonucleotides to target sequences can be carried out under conditions of reduced stringency, medium stringency or even stringent conditions. Suitable conditions for achieving reduced, medium and stringent hybridization conditions are as described herein.

Alternatively stated, in particular embodiments, antisense oligonucleotides of the invention have at least about 60%, 70%, 80%, 90%, 95%, 97%, 98% or higher sequence identity with the complement of the target sequence and reduce production of the protein product (as defined above). In some embodiments, the antisense sequence contains 1, 2, 3, 4, 5, 6, 7, 8, 9 or 10 mismatches as compared with the target sequence.

Methods of determining percent identity of nucleic acid sequences are described in more detail elsewhere herein.

The length of the antisense oligonucleotide is not critical as long as it specifically hybridizes to the intended target and reduces production of the protein product (as defined above) and can be determined in accordance with routine procedures. In general, the antisense oligonucleotide is at least about eight, ten or twelve or fifteen nucleotides in length and/or less than about 20, 30, 40, 50, 60, 70, 80, 100 or 150 nucleotides in length.

RNA interference (RNAi) is another useful approach for reducing production of a protein product (e.g., shRNA or siRNA). RNAi is a mechanism of post-transcriptional gene silencing in which double-stranded RNA (dsRNA) corresponding to a target sequence of interest is introduced into a cell or an organism, resulting in degradation of the corresponding mRNA. The mechanism by which RNAi achieves gene silencing has been reviewed in Sharp et al., (2001) *Genes Dev* 15: 485-490; and Hammond et al., (2001) *Nature Rev. Gen.* 2:110-119). The RNAi effect persists for multiple cell divisions before gene expression is regained. RNAi is therefore a powerful method for making targeted knockouts or "knockdowns" at the RNA level. RNAi has proven successful in human cells, including human embryonic kidney and HeLa cells (see, e.g., Elbashir et al., *Nature* (2001) 411:494-8).

Initial attempts to use RNAi in mammalian cells resulted in antiviral defense mechanisms involving PKR in response to the dsRNA molecules (see, e.g., Gil et al., (2000) *Apoptosis* 5:107). It has since been demonstrated that short synthetic dsRNA of about 21 nucleotides, known as "short interfering RNAs" (siRNA) can mediate silencing in mammalian cells without triggering the antiviral response (see, e.g., Elbashir et al., *Nature* (2001) 411:494-8; Caplen et al., (2001) *Proc. Nat. Acad. Sci. USA* 98:9742).

The RNAi molecule (including an siRNA molecule) can be a short hairpin RNA (shRNA; see Paddison et al., (2002), *Proc. Nat. Acad. Sci. USA* 99:1443-1448), which is believed to be processed in the cell by the action of the RNase III like enzyme Dicer into 20-25 mer siRNA molecules. The shRNAs generally have a stem-loop structure in which two inverted repeat sequences are separated by a short spacer sequence that loops out. There have been reports of shRNAs with loops ranging from 3 to 23 nucleotides in length. The loop sequence is generally not critical. Exemplary loop sequences include the following motifs: AUG, CCC, UUCG, CCACC, CTCGAG, AAGCUU, CCACACC and UUCAAGAGA.

The RNAi can further comprise a circular molecule comprising sense and antisense regions with two loop regions on either side to form a "dumbbell" shaped structure upon dsRNA formation between the sense and antisense regions. This molecule can be processed in vitro or in vivo to release the dsRNA portion, e.g., a siRNA.

International patent publication WO 01/77350 describes a vector for bidirectional transcription to generate both sense and antisense transcripts of a heterologous sequence in a eukaryotic cell. This technique can be employed to produce RNAi for use according to the invention.

Shinagawa et al., (2003) *Genes Dev.* 17:1340 reported a method of expressing long dsRNAs from a CMV promoter (a pol II promoter), which method is also applicable to tissue specific pol II promoters. Likewise, the approach of Xia et al., (2002) *Nature Biotech.* 20:1006, avoids poly(A) tailing and can be used in connection with tissue-specific promoters.

Methods of generating RNAi include chemical synthesis, in vitro transcription, digestion of long dsRNA by Dicer (in vitro or in vivo), expression in vivo from a delivery vector, and expression in vivo from a PCR-derived RNAi expression cassette (see, e.g., TechNotes 10(3) "Five Ways to Produce siRNAs," from Ambion, Inc., Austin Tex.

Guidelines for designing siRNA molecules are available (see e.g., literature from Ambion, Inc., Austin Tex.). In particular embodiments, the siRNA sequence has about 30-50% G/C content. Further, long stretches of greater than four T or A residues are generally avoided if RNA polymerase III is used to transcribe the RNA. Online siRNA target finders are available, e.g., from Ambion, Inc., through the Whitehead Institute of Biomedical Research or from Dharmacon Research, Inc.

The antisense region of the RNAi molecule can be completely complementary to the target sequence, but need not be as long as it specifically hybridizes to the target sequence (as defined above) and reduces production of the protein product (e.g., by at least about 30%, 40%, 50%, 60%, 70%, 80%, 90%, 95% or more). In some embodiments, hybridization of such oligonucleotides to target sequences can be carried out under conditions of reduced stringency, medium stringency or even stringent conditions, as defined above.

In other embodiments, the antisense region of the RNAi has at least about 60%, 70%, 80%, 90%, 95%, 97%, 98% or higher sequence identity with the complement of the target sequence and reduces production of the protein product (e.g., by at least about 30%, 40%, 50%, 60%, 70%, 80%, 90%, 95% or more). In some embodiments, the antisense region contains 1, 2, 3, 4, 5, 6, 7, 8, 9 or 10 mismatches as compared with the target sequence. Mismatches are generally tolerated better at the ends of the dsRNA than in the center portion.

In particular embodiments, the RNAi is formed by intermolecular complexing between two separate sense and antisense molecules. The RNAi comprises a ds region formed by the intermolecular basepairing between the two separate strands. In other embodiments, the RNAi comprises a ds region formed by intramolecular basepairing within a single nucleic acid molecule comprising both sense and antisense regions, typically as an inverted repeat (e.g., a shRNA or other stem loop structure, or a circular RNAi molecule). The RNAi can further comprise a spacer region between the sense and antisense regions.

Generally, RNAi molecules are highly selective. If desired, those skilled in the art can readily eliminate candidate RNAi that are likely to interfere with expression of nucleic acids other than the target by searching relevant databases to identify RNAi sequences that do not have substantial sequence homology with other known sequences, for example, using BLAST.

Kits for the production of RNAi are commercially available, e.g., from New England Biolabs, Inc. and Ambion, Inc.

The recombinant virus vector may also comprise a heterologous nucleotide sequence that shares homology with and recombines with a locus on the host chromosome. This approach may be utilized to correct a genetic defect in the host cell.

The present invention also provides recombinant virus vectors that express an immunogenic polypeptide, e.g., for vaccination. The heterologous nucleic acid may encode any immunogen of interest known in the art including, but are not limited to, immunogens from human immunodeficiency virus, influenza virus, gag proteins, tumor antigens, cancer antigens, bacterial antigens, viral antigens, and the like. Alternatively, the immunogen can be presented in the virus capsid (e.g., incorporated therein) or tethered to the virus capsid (e.g., by covalent modification).

The use of parvoviruses as vaccines is known in the art (see, e.g., Miyamura et al., (1994) *Proc. Nat. Acad. Sci. USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.; the disclosures of which are incorporated herein in their entireties by reference). The antigen may be presented in the virus capsid. Alternatively, the antigen may be expressed from a heterologous nucleic acid introduced into a recombinant vector genome.

An immunogenic polypeptide, or immunogen, may be any polypeptide suitable for protecting the subject against a disease, including but not limited to microbial, bacterial, protozoal, parasitic, fungal and viral diseases. For example, the immunogen may be an orthomyxovirus immunogen (e.g., an influenza virus immunogen, such as the influenza virus hemagglutinin (HA) surface protein or the influenza virus nucleoprotein gene, or an equine influenza virus immunogen), or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogen may also be an arenavirus immunogen (e.g., Lassa fever virus immunogen, such as the Lassa fever virus nucleocapsid protein gene and the Lassa fever envelope glycoprotein gene), a poxvirus immunogen (e.g., vaccinia, such as the vaccinia L1 or L8 genes), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS viruses), or a coronavirus immunogen (e.g., an infectious human coronavirus immunogen, such as the human coronavirus envelope glycoprotein gene, or a porcine transmissible gastroenteritis virus immunogen, or an avian infectious bronchitis virus immunogen, or a severe acute respiratory syndrome (SARS) immunogen such as a S [S1 or S2], M, E, or N protein or an immunogenic fragment thereof). The immunogen may further be a polio immunogen, herpes immunogen (e.g., CMV, EBV, HSV immunogens) mumps immunogen, measles immunogen, rubella immunogen, diphtheria toxin or other diphtheria immunogen, pertussis antigen, hepatitis (e.g., hepatitis A, hepatitis B or hepatitis C) immunogen, or any other vaccine immunogen known in the art.

Alternatively, the immunogen may be any tumor or cancer cell antigen. Optionally, the tumor or cancer antigen is expressed on the surface of the cancer cell. Exemplary cancer and tumor cell antigens are described in S. A. Rosenberg, (1999) *Immunity* 10:281). Illustrative cancer and tumor antigens include, but are not limited to: BRCA1 gene product, BRCA2 gene product, gp100, tyrosinase, GAGE-1/2, BAGE, RAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.*, 180:347; Kawakami et al., (1994) *Cancer Res.* 54:3124) including MART-1 (Coulie et al., (1991) *J. Exp. Med.* 180:35), gp100 (Wick et al., (1988) *J. Cutan. Pathol.* 4:201) and MAGE antigen (MAGE-1, MAGE-2 and MAGE-3) (Van der Bruggen et al., (1991) *Science,* 254: 1643), CEA, TRP-1; TRP-2; P-15 and tyrosinase (Brichard et al., (1993) *J. Exp. Med.* 178:489); HER-2/neu gene product (U.S. Pat. No. 4,968,603); CA 125; HE4; LK26; FB5 (endosialin); TAG 72; AFP; CA19-9; NSE; DU-PAN-2; CA50; Span-1; CA72-4; HCG; STN (sialyl Tn antigen); c-erbB-2 proteins; PSA; L-CanAg; estrogen receptor; milk fat globulin; p53 tumor suppressor protein (Levine, (1993) *Ann. Rev. Biochem.* 62:623); mucin antigens (international patent publication WO 90/05142); telomerases; nuclear matrix proteins; prostatic acid phosphatase; papilloma virus antigens; and antigens associated with the following cancers: melanomas, adenocarcinoma, thymoma, sarcoma, lung cancer, liver cancer, colorectal cancer, non-Hodgkin's lymphoma, Hodgkin's lymphoma, leukemias, uterine cancer, breast cancer, prostate cancer, ovarian cancer, cervical cancer, bladder cancer, kidney cancer, pancreatic cancer, brain cancer, kidney cancer, stomach cancer, esophageal cancer, head and neck cancer and others (see, e.g., Rosenberg, (1996) *Annu. Rev. Med.* 47:481-91).

Alternatively, the heterologous nucleotide sequence may encode any polypeptide that is desirably produced in a cell in vitro, ex vivo, or in vivo. For example, the virus vectors may be introduced into cultured cells and the expressed protein product isolated therefrom.

It will be understood by those skilled in the art that the heterologous polynucleotide(s) of interest may be operably associated with appropriate control sequences. For example, the heterologous nucleic acid may be operably associated with expression control elements, such as transcription/translation control signals, origins of replication, polyadenylation signals, internal ribosome entry sites (IRES), promoters, enhancers, and the like.

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

The present invention further provides methods of producing the virus vectors of the invention. In a representative embodiment, the present invention provides a method of producing a recombinant virus vector, the method comprising providing to a cell in vitro, (a) a template comprising (i) a polynucleotide of interest, and (ii) packaging signal sequences sufficient for the encapsidation of the AAV template into virus particles (e.g., one or more (e.g., two) terminal repeats, such as AAV terminal repeats), and (b) AAV sequences sufficient for replication and encapsidation of the template into viral particles (e.g., the AAV rep and AAV cap sequences). The template and AAV replication and capsid sequences are provided under conditions such that recombinant virus particles comprising the template packaged within the capsid are produced in the cell. The method can further comprise the step of collecting the virus particles from the cell. Virus particles may be collected from the medium and/or by lysing the cells.

In one illustrative embodiment, the invention provides a method of producing a rAAV particle comprising an AAV capsid, the method comprising: providing a cell in vitro with a nucleic acid encoding an AAV capsid, an AAV rep coding sequence, an AAV vector genome comprising a polynucleotide of interest, and helper functions for generating a productive AAV infection; and allowing assembly of the AAV particles comprising the AAV capsid and encapsidating the AAV vector genome.

The cell is typically a cell that is permissive for AAV viral replication. Any suitable cell known in the art may be employed, such as mammalian cells. Also suitable are trans-complementing packaging cell lines that provide functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an EBV based nuclear episome.

As a further alternative, the rep/cap sequences may be stably carried (episomal or integrated) within a cell.

Typically, the AAV rep/cap sequences will not be flanked by the AAV packaging sequences (e.g., AAV ITRs), to prevent rescue and/or packaging of these sequences.

The template (e.g., an rAAV vector genome) can be provided to the cell using any method known in the art. For example, the template may be supplied by a non-viral (e.g., plasmid) or viral vector. In particular embodiments, the template is supplied by a herpesvirus or adenovirus vector (e.g., inserted into the E1a or E3 regions of a deleted adenovirus). As another illustration, Palombo et al., (1998) *J. Virol.* 72:5025, describe a baculovirus vector carrying a reporter gene flanked by the AAV ITRs. EBV vectors may also be employed to deliver the template, as described above with respect to the rep/cap genes.

In another representative embodiment, the template is provided by a replicating rAAV virus. In still other embodiments, an AAV provirus is stably integrated into the chromosome of the cell.

To obtain maximal virus titers, helper virus functions (e.g., adenovirus or herpesvirus) essential for a productive AAV infection are generally provided to the cell. Helper virus sequences necessary for AAV replication are known in the art. Typically, these sequences are provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes required for efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper genes integrated in the chromosome or maintained as a stable extrachromosomal element. In representative embodiments, the helper virus sequences cannot be packaged into AAV virions, e.g., are not flanked by AAV ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct, but is optionally a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further contains the rAAV template. The AAV rep/cap sequences and/or the rAAV template may be inserted into a deleted region (e.g., the E1a or E3 regions) of the adenovirus.

In a further embodiment, the AAV rep/cap sequences and the adenovirus helper sequences are supplied by a single adenovirus helper vector. The rAAV template is provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as a "EBV based nuclear episome," see Margolski, (1992) *Curr. Top. Microbiol. Immun.* 158:67).

In a further exemplary embodiment, the AAV rep/cap sequences and adenovirus helper sequences are provided by a single adenovirus helper. The rAAV template is provided as a separate replicating viral vector. For example, the rAAV template may be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, in representative embodiments, the adenovirus helper sequences and the AAV rep/cap sequences are not flanked by the AAV packaging sequences (e.g., the AAV ITRs), so that these sequences are not packaged into the AAV virions.

Herpesvirus may also be used as a helper virus in AAV packaging methods. Hybrid herpesviruses encoding the AAV rep protein(s) may advantageously facilitate for more scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377, the disclosures of which are incorporated herein in their entireties).

As a further alternative, the virus vectors of the invention can be produced in insect cells using baculovirus vectors to deliver the rep/cap genes and rAAV template as described by Urabe et al., (2002) *Human Gene Therapy* 13:1935-43.

Other methods of producing AAV use stably transformed packaging cells (see, e.g., U.S. Pat. No. 5,658,785).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al., (1999) *Gene Therapy* 6:973). In representative embodiments, deleted replication-defective helper viruses are used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

The inventive packaging methods may be employed to produce high titer stocks of virus particles. In particular embodiments, the virus stock has a titer of at least about $10^5$ transducing units (tu)/ml, at least about $10^6$ tu/ml, at least about $10^7$ tu/ml, at least about $10^8$ tu/ml, at least about $10^9$ tu/ml, or at least about $10^{10}$ tu/ml.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a polynucleotide of interest to a cell in vitro. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the virus vector can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell (cancers and tumors are described above). Moreover, the cells can be from any species of origin, as indicated above.

The virus vectors may be introduced to cells in vitro for the purpose of administering the modified cell to a subject. In particular embodiments, the cells have been removed from a subject, the virus vector is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the recombinant virus vector is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

In some embodiments, cells that have been transduced with the virus vector may be administered to elicit an immunogenic response against the delivered polypeptide (e.g., expressed as a transgene or in the capsid). Typically, a quantity of cells expressing an effective amount of the polypeptide in combination with a pharmaceutically acceptable carrier is administered. Optionally, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vectors of the invention to subjects. In particular embodiments, the method comprises a method of delivering a polynucleotide of interest to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

The virus vectors of the invention can further be administered to a subject to elicit an immunogenic response (e.g., as a vaccine). Typically, vaccines of the present invention comprise an effective amount of virus in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$ transducing units or more, preferably about $10^7$ or $10^8$, $10^9$, $10^{10}$, $10^{11}$, $10^{12}$, $10^{13}$, $10^{14}$, $10^{15}$, $10^{16}$ transducing units, yet more preferably about $10^{12}$ to $10^{14}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or a near a tumor or a lymph node). The most suitable route in any given case will depend on the nature and severity of the condition being treated and on the nature of the particular vector that is being used.

Delivery to any of these tissues can also be achieved by delivering a depot comprising the virus vector, which can be implanted into the tissue or the tissue can be contacted with a film or other matrix comprising the virus vector. Examples of such implantable matrices or substrates are described in U.S. Pat. No. 7,201,898).

The invention can be used to treat disorders of a tissue or organ. Alternatively, the invention can be practiced to deliver a nucleic acid to a tissue or organ, which is used as a platform for production of a protein product (e.g., an enzyme) or non-translated RNA (e.g., RNAi, microRNA, antisense RNA) that normally circulates in the blood or for systemic delivery to other tissues to treat a disorder (e.g., a metabolic disorder, such as diabetes (e.g., insulin), hemophilia (e.g., Factor IX or Factor VIII), or a lysosomal storage disorder (such as Gaucher's disease [glucocerebrosidase], Pompe disease [lysosomal acid α-glucosidase] or Fabry disease [α-galactosidase A]) or a glycogen storage disorder (such as Pompe disease [lysosomal acid α glucosidase]). Other suitable proteins for treating metabolic disorders are described above.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multidose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Production of Factor IX Proteins of this Invention

Many expression vectors can be used to create genetically engineered cells. Some expression vectors are designed to express large quantities of recombinant proteins after amplification of transfected cells under a variety of conditions that favor selected, high expressing cells. Some expression vectors are designed to express large quantities of recombinant proteins without the need for amplification under selection pressure. The present invention includes the production of genetically engineered cells according to methods standard in the art and is not dependent on the use of any specific expression vector or expression system.

To create a genetically engineered cell to produce large quantities of a FIX protein, cells are transfected with an expression vector that contains a polynucleotide (e.g., cDNA) encoding the protein. In some embodiments, the FIX protein is expressed with selected co-transfected enzymes that cause proper post-translational modification of the FIX protein to occur in a given cell system.

The cell may be selected from a variety of sources, but is otherwise a cell that may be transfected with an expression vector containing a nucleic acid molecule (e.g., a cDNA) encoding a FIX protein.

The practice of the present invention employs, unless otherwise indicated, conventional techniques of molecular biology, microbiology, recombinant DNA, and immunology, which are within the skill of the art. Such techniques are explained fully in the literature. See, e.g., Sambrook, et al., *Molecular Cloning; A Laboratory Manual,* 2nd ed. (1989); *DNA Cloning*, Vols. I and II (D. N Glover, ed. 1985); *Oligonucleotide Synthesis* (M. J. Gait, ed. 1984); *Nucleic Acid Hybridization* (B. D. Hames & S. J. Higgins, eds. 1984); *Transcription and Translation* (B. D. Hames & S. J. Higgins, eds. 1984); *Animal Cell Culture* (R. I. Freshney, ed. 1986); *Immobilized Cells and Enzymes* (IRL Press, 1986); B. Perbal, *A Practical Guide to Molecular Cloning* (1984); the series, *Methods in Enzymology* (Academic Press, Inc.), particularly Vols. 154 and 155 (Wu and Grossman, and Wu, eds., respectively); *Gene Transfer Vectors for Mammalian Cells* (J. H. Miller and M. P. Calos, eds. 1987, Cold Spring Harbor Laboratory); *Immunochemical Methods in Cell and*

Molecular Biology, Mayer and Walker, eds. (Academic Press, London, 1987); Scopes, Protein Purification: Principles and Practice, 2nd ed. 1987 (Springer-Verlag, N.Y.); and Handbook of Experimental Immunology Vols I-IV (D. M. Weir and C. C. Blackwell, eds. 1986). All patents, patent applications, and publications cited in the specification are incorporated herein by reference in their entireties.

Genetic Engineering Techniques

The production of cloned genes, recombinant DNA, vectors, transformed cells, proteins and protein fragments by genetic engineering is well known. See, e.g., U.S. Pat. No. 4,761,371 to Bell et al. at Col. 6, line 3 to Col. 9, line 65; U.S. Pat. No. 4,877,729 to Clark et al. at Col. 4, line 38 to Col. 7, line 6; U.S. Pat. No. 4,912,038 to Schilling at Col. 3, line 26 to Col. 14, line 12; and U.S. Pat. No. 4,879,224 to Wallner at Col. 6, line 8 to Col. 8, line 59.

A vector is a replicable DNA construct. Vectors are used herein either to amplify nucleic acid encoding FIX protein and/or to express nucleic acid which encodes FIX protein. An expression vector is a replicable nucleic acid construct in which a nucleotide sequence encoding a FIX protein is operably linked to suitable control sequences capable of effecting the expression of the nucleotide sequence to produce a FIX protein in a suitable host cell. The need for such control sequences will vary depending upon the host cell selected and the transformation method chosen. Generally, control sequences include a transcriptional promoter, an optional operator sequence to control transcription, a sequence encoding suitable mRNA ribosomal binding sites, and sequences that control the termination of transcription and translation.

Vectors comprise plasmids, viruses (e.g., AAV, adenovirus, cytomegalovirus), phage, and integratable DNA fragments (i.e., fragments integratable into the host cell genome by recombination). The vector can replicates and function independently of the host cell genome (e.g., via transient expression), or can integrate into the host cell genome itself (e.g., stable integration). Expression vectors can contain a promoter and RNA binding sites that are operably linked to the nucleic acid molecule to be expressed and are operable in the host cell and/or organism.

DNA regions or nucleotide sequences are operably linked or operably associated when they are functionally related to each other. For example, a promoter is operably linked to a coding sequence if it controls the transcription of the sequence; or a ribosome binding site is operably linked to a coding sequence if it is positioned so as to permit translation of the sequence.

Suitable host cells include prokaryote, yeast or higher eukaryotic cells such as mammalian cells and insect cells. Cells derived from multicellular organisms are a particularly suitable host for recombinant FIX protein synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines, and WI138, HEK 293, BHK, COS-7, CV, and MDCK cell lines. Expression vectors for such cells ordinarily include (if necessary) an origin of replication, a promoter located upstream from the nucleotide sequence encoding FIX protein to be expressed and operatively associated therewith, along with a ribosome binding site, an RNA splice site (if intron-containing genomic DNA is used), a polyadenylation site, and a transcriptional termination sequence. In one embodiment, expression can be carried out in Chinese Hamster Ovary (CHO) cells using the expression system of U.S. Pat. No. 5,888,809, which is incorporated herein by reference in its entirety.

The transcriptional and translational control sequences in expression vectors to be used in transforming vertebrate cells are often provided by viral sources. Nonlimiting examples include promoters derived from polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV 40 or other viral (e.g., polyoma, adenovirus, VSV, or BPV) source, or may be provided by the host cell chromosomal replication mechanism. If the vector is integrated into the host cell chromosome, the latter is often sufficient.

Rather than using vectors that contain a viral origin of replication, one can transform mammalian cells by the method of cotransformation with a selectable marker and the nucleic acid molecule encoding the FIX protein. Nonlimiting examples of suitable selectable markers are dihydrofolate reductase (DHFR) or thymidine kinase. This method is further described in U.S. Pat. No. 4,399,216 which is incorporated by reference herein in its entirety.

Other methods suitable for adaptation to the synthesis of FIX protein in recombinant vertebrate cell culture include those described in Gething et al. Nature 293:620 (1981); Mantei et al. Nature 281:40; and Levinson et al., EPO Application Nos. 117,060A and 117,058A, the entire contents of each of which are incorporated herein by reference.

Host cells such as insect cells (e.g., cultured Spodoptera frugiperda cells) and expression vectors such as the baculovirus expression vector (e.g., vectors derived from Autographa californica MNPV, Trichoplusia ni MNPV, Rachiplusia ou MNPV, or Galleria ou MNPV) may be employed in carrying out the present invention, as described in U.S. Pat. Nos. 4,745,051 and 4,879,236 to Smith et al. In general, a baculovirus expression vector comprises a baculovirus genome containing the nucleotide sequence to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example Escherichia coli (E. coli) or bacilli, respectively. Higher eukaryotic cells include established cell lines of mammalian origin as described herein. Exemplary bacterial host cells are E. coli W3110 (ATCC 27,325), E. coli B, E. coli X1776 (ATCC 31,537) and E. coli 294 (ATCC 31,446). A broad variety of suitable prokaryotic and microbial vectors are available. E. coli is typically transformed using pBR322. Promoters most commonly used in recombinant microbial expression vectors include the betalactamase (penicillinase) and lactose promoter systems (Chang et al. Nature 275:615 (1978); and Goeddel et al. Nature 281:544 (1979)), a tryptophan (trp) promoter system (Goeddel et al. Nucleic Acids Res. 8:4057 (1980) and EPO App. Publ. No. 36,776) and the tac promoter (De Boer et al. Proc. Natl. Acad. Sci. USA 80:21 (1983)). The promoter and Shine-Dalgarno sequence (for prokaryotic host expression) are operably linked to the nucleic acid encoding the FIX protein, i.e., they are positioned so as to promote transcription of FIX messenger RNA from DNA.

Eukaryotic microbes such as yeast cultures may also be transformed with protein-encoding vectors (see, e.g., U.S. Pat. No. 4,745,057). Saccharomyces cerevisiae is the most commonly used among lower eukaryotic host microorganisms, although a number of other strains are commonly available. Yeast vectors may contain an origin of replication from the 2 micron yeast plasmid or an autonomously replicating sequence (ARS), a promoter, nucleic acid encoding FIX protein, sequences for polyadenylation and transcription termination, and a selection gene. An exemplary plasmid is YRp7, (Stinchcomb et al. *Nature* 282:39 (1979); Kingsman et al. *Gene* 7:141 (1979); Tschemper et al. *Gene* 10:157 (1980)). Suitable promoting sequences in yeast vectors include the promoters for metallothionein, 3-phosphoglycerate kinase (Hitzeman et al. *J. Biol. Chem.* 255:2073 (1980) or other glycolytic enzymes (Hess et al. *J. Adv. Enzyme Reg.* 7:149 (1968); and Holland et al. *Biochemistry* 17:4900 (1978)). Suitable vectors and promoters for use in yeast expression are further described in R. Hitzeman et al., EPO Publn. No. 73,657.

Cloned coding sequences of the present invention may encode FIX of any species of origin, including mouse, rat, dog, opossum, rabbit, cat, pig, horse, sheep, cow, guinea pig, opossum, platypus, and human, but preferably encode FIX protein of human origin. Nucleic acid encoding FIX that is hybridizable with nucleic acid encoding proteins disclosed herein is also encompassed. Hybridization of such sequences may be carried out under conditions of reduced stringency or even stringent conditions (e.g., stringent conditions as represented by a wash stringency of 0.3M NaCl, 0.03M sodium citrate, 0.1% SDS at 60° C. or even 70° C.) to nucleic acid encoding FIX protein disclosed herein in a standard in situ hybridization assay. See, e.g., Sambrook et al., *Molecular Cloning, A Laboratory Manual* (2d Ed. 1989) Cold Spring Harbor Laboratory).

The FIX proteins produced according to the invention may be expressed in transgenic animals by known methods. See for example, U.S. Pat. No. 6,344,596, which is incorporated herein by reference in its entirety. In brief, transgenic animals may include but are not limited to farm animals (e.g., pigs, goats, sheep, cows, horses, rabbits and the like) rodents (such as mice, rats and guinea pigs), and domestic pets (for example, cats and dogs). Livestock animals such as pigs, sheep, goats and cows, are particularly preferred in some embodiments.

The transgenic animal of this invention is produced by introducing into a single cell embryo an appropriate polynucleotide that encodes a human FIX protein of this invention in a manner such that the polynucleotide is stably integrated into the DNA of germ line cells of the mature animal, and is inherited in normal Mendelian fashion. The transgenic animal of this invention would have a phenotype of producing the FIX protein in body fluids and/or tissues. The FIX protein would be removed from these fluids and/or tissues and processed, for example for therapeutic use. (See, e.g., Clark et al. "Expression of human anti-hemophilic factor IX in the milk of transgenic sheep" *Bio/Technology* 7:487-492 (1989); Van Cott et al. "Haemophilic factors produced by transgenic livestock: abundance can enable alternative therapies worldwide" *Haemophilia* 10(4):70-77 (2004), the entire contents of which are incorporated by reference herein).

DNA molecules can be introduced into embryos by a variety of means including but not limited to microinjection, calcium phosphate mediated precipitation, liposome fusion, or retroviral infection of totipotent or pluripotent stem cells. The transformed cells can then be introduced into embryos and incorporated therein to form transgenic animals. Methods of making transgenic animals are described, for example, in *Transgenic Animal Generation and Use* by L. M. Houdebine, Harwood Academic Press, 1997. Transgenic animals also can be generated using methods of nuclear transfer or cloning using embryonic or adult cell lines as described for example in Campbell et al., *Nature* 380:64-66 (1996) and Wilmut et al., *Nature* 385:810-813 (1997). Further a technique utilizing cytoplasmic injection of DNA can be used as described in U.S. Pat. No. 5,523,222.

FIX-producing transgenic animals can be obtained by introducing a chimeric construct comprising FIX-encoding sequences. Methods for obtaining transgenic animals are well-known. See, for example, Hogan et al., *MANIPULATING THE MOUSE EMBRYO*, (Cold Spring Harbor Press 1986); Krimpenfort et al., *Bio/Technology* 9:88 (1991); Palmiter et al., *Cell* 41:343 (1985), Kraemer et al., *GENETIC MANIPULATION OF THE EARLY MAMMALIAN EMBRYO*, (Cold Spring Harbor Laboratory Press 1985); Hammer et al., *Nature* 315:680 (1985); Wagner et al., U.S. Pat. No. 5,175,385; Krimpenfort et al., U.S. Pat. No. 5,175,384, Janne et al., *Ann. Med.* 24:273 (1992), Brem et al., *Chim. Oggi.* 11:21 (1993), Clark et al., U.S. Pat. No. 5,476,995, all incorporated by reference herein in their entireties.

In some embodiments, cis-acting regulatory regions may be used that are "active" in mammary tissue in that the promoters are more active in mammary tissue than in other tissues under physiological conditions where milk is synthesized. Such promoters include but are not limited to the short and long whey acidic protein (WAP), short and long α, β and κ casein, α-lactalbumin and β-lactoglobulin ("BLG") promoters. Signal sequences can also be used in accordance with this invention that direct the secretion of expressed proteins into other body fluids, particularly blood and urine. Examples of such sequences include the signal peptides of secreted coagulation factors including signal peptides of FIX, protein C, and tissue-type plasminogen activator.

Among the useful sequences that regulate transcription, in addition to the promoters discussed above, are enhancers, splice signals, transcription termination signals, polyadenylation sites, buffering sequences, RNA processing sequences and other sequences which regulate the expression of transgenes.

Preferably, the expression system or construct includes a 3' untranslated region downstream of the nucleotide sequence encoding the desired recombinant protein. This region can increase expression of the transgene. Among the 3' untranslated regions useful in this regard are sequences that provide a poly A signal.

Suitable heterologous 3'-untranslated sequences can be derived, for example, from the SV40 small t antigen, the casein 3' untranslated region, or other 3' untranslated sequences well known in this art. Ribosome binding sites are also important in increasing the efficiency of expression of FIX. Likewise, sequences that regulate the post-translational modification of FIX are useful in the invention.

Having described the present invention, the same will be explained in greater detail in the following examples, which are included herein for illustration purposes only, and which are not intended to be limiting to the invention.

EXAMPLE 1

Construction of Gene Expression Cassettes

To increase human factor IX gene expression efficiency and longevity, we have made a number of efforts to achieve the goal: 1) to obtain liver specificity and strong activity by synthesizing a number of designer promoters; 2) to increase the efficiency of transgene mRNA processing by using a small intron following the promoter; and de novo insertion of a second small intron in the protein coding region of the gene; 3) to increase the translation efficiency for transgene product protein synthesis by optimizing the 5' untranslated sequences for reduced secondary structure, etc.; 4) to optimize human codon usage and reduce the CpG motifs and reduce long G and C tracks; 5) to use a bidirectional polyadenylation sequence for efficient polyA synthesis and blockade of the residue anti-sense promoter activity from the 3' inverted terminal repeat (ITR) of AAV.

We have designed and fully synthesized a number of artificial promoters that contain a conserved basal promoter element and transcription initiation site. The basal promoter is linked at its 5' end with a number of liver-specific transcriptional factor binding sites for liver-specific expression. A promoter named LXP2.1 (FIG. 1) (SEQ ID NO:1) was selected due to its small size (188 bp) and high activity initially screened in vitro using a luciferase reporter gene and transfection experiments in human liver cancer cell line Huh7 (Table 4). We further examined the LXP2.1 promoter with the ubiquitous and strong CMV promoter in vivo after packaging the Gaussia luciferase expression cassette in AAV8 viral particles and injected in mouse tail vein. The luciferase expression was assayed using sera taken from the mice 2 weeks after IV injection of $5 \times 10^{10}$ vector genome (v.g.)/mouse (Table 5). The LXP2.1 promoter was about 4 times as strong as the CMV promoter.

TABLE 4

| Promoter | Luciferase activity (light units/mg protein) |
|---|---|
| CMV-Gluc (promoter 600 bp) | $2.4 \times 10^6$ |
| LXP2.1-Gluc (promoter 194 bp) | $3.52 \times 10^5$ |

TABLE 5

| Promoter | Luciferase activity/µl serum |
|---|---|
| AAV8-CMV-Gluc | 22,543 ± 15,308 |
| AAV8-LXP2.1-Gluc | 82,240 ± 23,045 |

To enhance factor IX gene expression in vivo, we have taken two approaches to achieve the goal. First, we have fully synthesized the coding sequence of the human factor gene using the human codon-optimization program of GeneArt (Invitrogen), with the purpose of maximizing the usage of the more effective codons. In addition, we have attempted to reduce or remove all of the CpG sequences in the synthetic factor IX gene. It has been documented that the CpG islands or motifs in the gene could induce innate immune responses (e.g., Toll-like receptor 9, TLR9, mediated immune responses (Bauer et al., *Proc. Natl. Acad. Sci. USA* 98(16):9237 (2001)) and also potentially cause gene silencing. In the factor IX gene-1 (SEQ ID NO:6) and factor IX gene-2 (SEQ ID NO:7), the CpG motifs were completely removed. However, in factor IX gene-3 (SEQ ID NO:8), only the TCG and CGT sequences were removed. It has been reported that in human cells, a conserved CpG motif, GTCGTT, is the most potent motif that triggers TLR9 responses. The removal of TCG and CGT motifs effectively abolished the GTCGTT element.

It has been well documented that introns exert their function by facilitating pre-mRNA processing and enhancing gene expression. The native introns of the human factor IX gene are relatively large in size and unsuitable for our gene expression cassette. In an attempt to further increase the factor IX gene expression, we synthesized small human introns (SEQ ID NOS:4 and 5). The first intron was inserted in an artificial 5' untranslated region (5' UTR) (SEQ ID NO:4) between AAG and G. The second intron (SEQ ID NO:5) was inserted into the 5' coding region of the gene between nucleotides CAG and G, a consensus exon/intron junction site. The complete DNA sequence of the above three genes with the artificial intron (SEQ ID NO:5) insertion were listed as SEQ ID NOS:6, 7 and 8, respectively. Although we did not examine insertion of artificial intron 1 in the coding sequence of the factor IX gene and/or insertion of intron 2 in the 5' UTR, we anticipate similar results could be obtained.

EXAMPLE 2

In Vitro Expression of Gene Expression Cassettes

To examine if the designer human factor IX gene expression cassettes work in cells, we transfected the above mentioned expression cassettes into the Huh7 cell line. Huh7 is often used to examine promoters that show activities in hepatocytes. As Huh7 cells do not produce any endogenous clotting factor IX, the non-transfected cells were used as a negative control. The purpose of this experiment was to see if our novel factor IX constructs can produce functional factor protein that is secreted extracellularly into the cell culture media in human cells. At 24 hours after transfection, the cell culture media were replaced with serum-free media and continued to culture for another 24 hours. Subsequently, the cell culture media were collected and subjected to the APTT test, a commonly used clotting activity test in vitro. Our results indicated that all of our constructs expressed and secreted high levels of factor IX protein (FIG. 3). The confirmation of functionality of our gene expression cassettes prompted us to carry out in vivo gene expression experiments in hemophilia B mice, a clinically relevant animal model.

EXAMPLE 3

In Vivo Expression of Gene Expression Cassettes

As in vitro cell culture transfection experiment suggested that the gene expression cassette harboring codon optimized human factor IX gene-1 with artificial intron-2 (SEQ ID NO:4) was more potent, we selected this construct flanked by AAV inverted terminal repeats (ITR) and packaged it into an AAV8 serotype vector, a robust liver-tropic AAV vector in mouse liver for high level expression. To investigate if the codon optimized human factor IX gene-1 works in other serotypes of AAV vector, we packaged it in a novel AAV vector with engineered capsid (AAVXL14). The vector was purified by double CsCl density ultracentrifugation, dialyzed against saline and titered by DNA dot blot and AAV capsid protein silver staining after PAGE gel separation. At the same time, a previously reported human factor IX gene expression cassette (Wu et al., *Mol. Ther.* 16(2):280 (2008)), named here as F9-ZWu, was packaged in AAV8 vector as a positive control. That cassette contained a liver-specific TTR promoter and a different codon-optimized human factor IX gene but harbored the same amino acid R338L mutation (the Padua mutation; Simioni et al., *N. Engl. J. Med* 361(17): 1671 (2009)).

To examine how efficient the factor IX expression cassettes perform in vivo, we chose to use six week old male factor IX gene knockout mice (commonly used hemophilia B animal model). The above mentioned vectors were intravenously injected via the tail vein in the factor IX KO mice at 4 different doses, $1\times10^{10}$ vg/kg (vector genomes/kilogram bodyweight), $4\times10^{10}$ vg/kg, $1\times10^{11}$ vg/kg and $4\times10^{11}$ vg/kg (Table 4). Untreated age- and sex-matched factor IX KO mice were used as negative control. Plasma were collected every 2 weeks via retroorbital vein using the standard protocol. Plasma samples were frozen at −80° C. for further testing. To quantitatively evaluate human factor IX gene expression, the plasma samples were subjected to a routine APTT test, using purified recombinant human factor IX serially diluted in the plasma of severe hemophilia B patients as the standard curve for factor IX activities.

Figure 4:
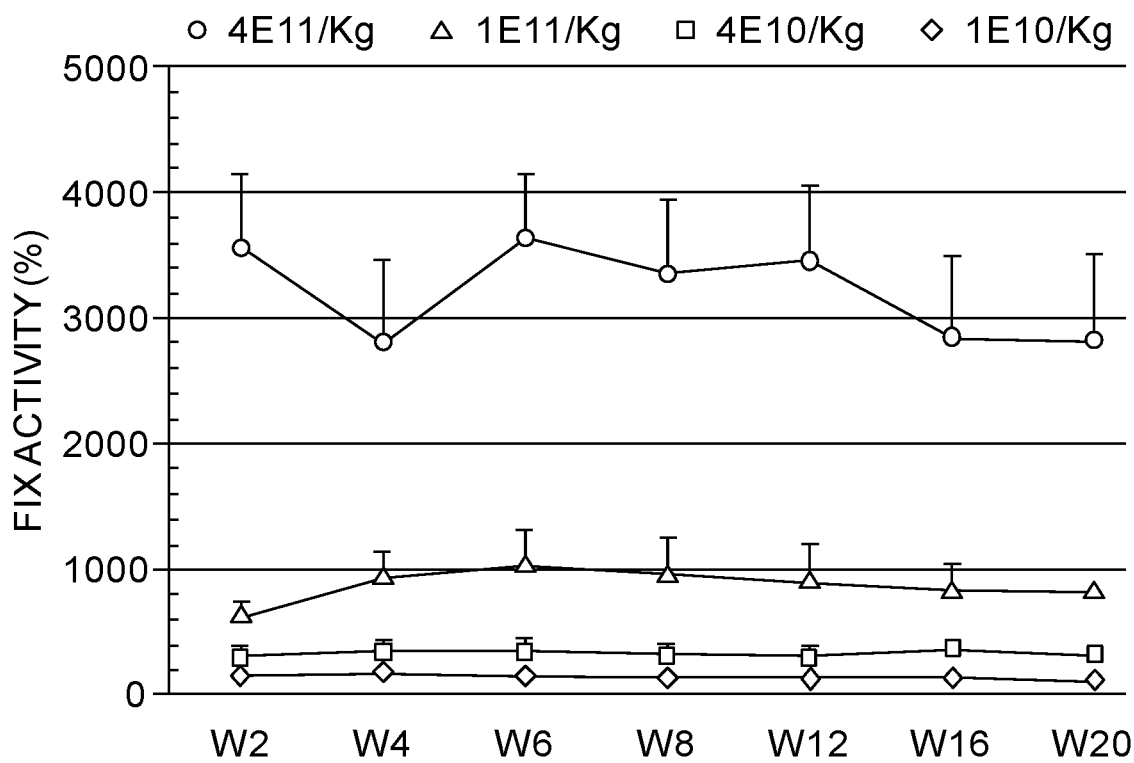
FIG. 4 shows robust and long-term factor IX expression and clotting activity assays after dose escalation of AAV8-LXP2.1-opti-FIX-1 vector in a FIX gene KO mouse model.

Our results showed that all AAV vectors expressed human factor IX in the KO mice (Table 6). However, our FIX gene-1 expression cassette was significantly more efficient than a previously reported positive-control vector F9-ZWu (Wu et al., Mol. Ther. 16(2):280 (2008)). For example, at the vector doses of $1\times110^{11}$ vg/kg and $4\times10^{11}$ vg/kg, our vector achieved an expression level that was approximately 25 and 34 time as high as the positive control vector. At a vector dose as low as $1\times10^{10}$ vg/kg body weight, our vector was able to achieve approximately 140% of the normal physiological levels of human factor activity. In addition, human factor gene expression at all doses tested was stable for up to 20 weeks (FIG. 4 and Table 7), which was the duration of the in vivo experiments. Our results thus demonstrated that the gene expression was not only robust but was also long term. Persistent high level expression of the FIX-1 gene product in FIX KO mice did not cause any discernible adverse effect.

TABLE 6

| Vector | $1\times10^{10}$ vg/kg | $4\times10^{10}$ vg/kg | $1\times10^{11}$ vg/kg | $4\times10^{11}$ vg/kg |
|---|---|---|---|---|
| AAV8.F9-1 | 140.2 ± 12.5 | 324.6 ± 64.2 | 624.2 ± 119.0 | 3557 ± 600 |
| AAVXL14 F9-1 | Not tested | 105.1 ± 22.2 | Not tested | 1651 ± 659 |
| AAV8-F9-ZWu | <1% | Not tested | 25.4 ± 16.7 | 105.3 ± 102.6 |

Factor IX activates were measured at 2 weeks post vector injection (n=7).

Factor IX activities were shown as a percentage of normal human plasma level.

TABLE 7

| Dose | W2 | W4 | W6 | W8 | W12 | W15 | W20 |
|---|---|---|---|---|---|---|---|
| $1\times10^{10}$ vg/kg | 140.3 ± 11.5 | 174.4 ± 24.9 | 142.7 ± 5.6 | 138.1 ± 4.7 | 122.0 ± 17.7 | 137.1 ± 30.0 | 97.1 ± 128.0 |
| $4\times10^{10}$ vg/kg | 324.7 ± 64.3 | 350.2 ± 81.3 | 354.0 ± 90.4 | 328.0 ± 64.5 | 318.0 ± 61.1 | 360.7 ± 152.0 | 319.2 ± 67.8 |
| $1\times10^{11}$ vg/kg | 624.0 ± 1110.5 | 939.9 ± 196.2 | 1023.2 ± 291.5 | 959.2 ± 290.8 | 889.6 ± 315.4 | 822.4 ± 220.1 | 808.6 ± 272.0 |
| $4\times10^{11}$ vg/kg | 3557.8 ± 600.6 | 2815.7 ± 655.2 | 3648.8 ± 503.0 | 3361.3 ± 578.6 | 3458.4 ± 593.5 | 2847.2 ± 650.3 | 2820.8 ± 696.4 |

Factor IX activities were shown as a percentage of normal human plasma level.

It will be understood by those of skill in the art that numerous and various modifications can be made without departing from the spirit of the present invention. Therefore, it should be clearly understood that the forms of the present invention are illustrative only and are not intended to limit the scope of the present invention.

All publications, patent applications, patents, patent publications, sequences identified by GenBank® database accession numbers and other references cited herein are incorporated by reference in their entireties for the teachings relevant to the sentence and/or paragraph in which the reference is presented.

The foregoing is illustrative of the present invention, and is not to be construed as limiting thereof. The invention is defined by the following claims, with equivalents of the claims to be included therein.

What is claimed is:

1. A polynucleotide comprising a synthetic liver-specific promoter, wherein the promoter comprises the nucleotide sequence of SEQ ID NO: 1.

2. The polynucleotide of claim 1, wherein the promoter is operably linked to a polynucleotide of interest.

3. The polynucleotide of claim 2, wherein the polynucleotide of interest encodes a polypeptide or a functional nucleic acid.

4. The polynucleotide of claim 3, wherein the polynucleotide of interest encodes a clotting factor.

5. The polynucleotide of claim 4, wherein the polynucleotide of interest encodes Factor IX.

6. The polynucleotide of claim 5, wherein the polynucleotide sequence has been codon optimized for expression in humans.

7. The polynucleotide of claim 5, wherein the polynucleotide of interest encoding Factor IX comprises a missense mutation resulting in a R338L mutation (numbering with respect to human Factor IX).

8. The polynucleotide of claim 2, further comprising a synthetic 5'-untranslated region between the promoter and the polynucleotide of interest.

9. The polynucleotide of claim 8, wherein the synthetic 5'-untranslated region comprises a synthetic intron.

10. The polynucleotide of claim 2, wherein the polynucleotide of interest comprises a synthetic intron.

11. The polynucleotide of claim 1, operably linked to a polyadenylation site.

12. The polynucleotide of claim 11, wherein the polyadenylation site is a bidirectional polyadenylation site.

13. A vector comprising the polynucleotide of claim 1.

14. A transformed cell comprising the polynucleotide of claim 1.

15. A pharmaceutical composition comprising the polynucleotide of claim 1 and a pharmaceutically acceptable carrier.

16. A method of producing a polypeptide or a functional nucleic acid in the liver of a subject, comprising delivering to the subject an effective amount of an adeno-associated virus (AAV) vector comprising the polynucleotide of claim 2, thereby producing the polypeptide or functional nucleic acid in the liver of the subject.

17. A method of treating hemophilia B or acquired Factor IX deficiency in a subject, comprising delivering to the subject a therapeutically effective amount of an adeno-associated virus (AAV) vector comprising the polynucleotide of claim 5, thereby treating hemophilia B in the subject.

18. A method of increasing the bioavailability of a Factor IX polypeptide in a subject, comprising delivering to the subject an effective amount of an adeno-associated virus (AAV) vector comprising the polynucleotide of claim 5, thereby increasing the bioavailability of the Factor IX polypeptide in the subject.

19. The polynucleotide of claim 1, comprising the nucleotide sequence of one of SEQ ID NOS: 10-12.

20. The vector of claim 13, wherein the vector is an adeno-associated virus (AAV) vector.

21. A polynucleotide encoding a human Factor IX that has been codon optimized for expression in humans, further comprising a synthetic intron, wherein the codon-optimized Factor IX encoding sequence and synthetic intron comprise the nucleotide sequence of one of SEQ ID NOS: 6-8.

22. A vector comprising the polynucleotide of claim 21.

23. The vector of claim 22, wherein the vector is an adeno-associated virus (AAV) vector.

24. A transformed cell comprising the polynucleotide of claim 21.

25. A pharmaceutical composition comprising the polynucleotide of claim 21 and a pharmaceutically acceptable carrier.

26. A method of treating hemophilia B or acquired Factor IX deficiency in a subject, comprising delivering to the subject a therapeutically effective amount of an adeno-associated virus (AAV) vector comprising the polynucleotide of claim 21, thereby treating hemophilia B in the subject.

* * * * *

UNITED STATES PATENT AND TRADEMARK OFFICE
CERTIFICATE OF CORRECTION

| | |
|---|---|
| PATENT NO. | : 11,530,402 B2 |
| APPLICATION NO. | : 16/616784 |
| DATED | : December 20, 2022 |
| INVENTOR(S) | : Xiao et al. |

It is certified that error appears in the above-identified patent and that said Letters Patent is hereby corrected as shown below:

In the Specification

Column 43, Line 21: Please correct "$1 \times 110^{11}$ vg/kg" to read --$1 \times 10^{11}$ vg/kg--

Signed and Sealed this
Eleventh Day of April, 2023

Katherine Kelly Vidal
*Director of the United States Patent and Trademark Office*